United States Patent
Scholler et al.

(10) Patent No.: US 9,708,384 B2
(45) Date of Patent: Jul. 18, 2017

(54) UNIVERSAL IMMUNE RECEPTOR EXPRESSED BY T CELLS FOR THE TARGETING OF DIVERSE AND MULTIPLE ANTIGENS

(71) Applicant: The Trustees of the University of Pennsylvania, Philadelphia, PA (US)

(72) Inventors: Nathalie Scholler, Narberth, PA (US); Katarzyna Urbanska, Philadelphia, PA (US); Daniel J. Powell, Jr., Bala Cynwyd, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 44 days.

(21) Appl. No.: 14/346,612

(22) PCT Filed: Sep. 24, 2012

(86) PCT No.: PCT/US2012/056901
§ 371 (c)(1),
(2) Date: Mar. 21, 2014

(87) PCT Pub. No.: WO2013/044225
PCT Pub. Date: Mar. 28, 2013

(65) Prior Publication Data
US 2014/0234348 A1    Aug. 21, 2014

Related U.S. Application Data

(60) Provisional application No. 61/537,933, filed on Sep. 22, 2011.

(51) Int. Cl.
| | | |
|---|---|---|
| *C12N 15/85* | (2006.01) | |
| *C12N 15/63* | (2006.01) | |
| *C07H 21/04* | (2006.01) | |
| *C07K 14/725* | (2006.01) | |
| *C07K 14/465* | (2006.01) | |
| *A61K 47/48* | (2006.01) | |
| *C07K 14/705* | (2006.01) | |

(52) U.S. Cl.
CPC .... *C07K 14/7051* (2013.01); *A61K 47/48776* (2013.01); *C07K 14/465* (2013.01); *C07K 14/70517* (2013.01); *C07K 14/70521* (2013.01); *C12N 15/85* (2013.01); *C07K 2319/00* (2013.01); *C07K 2319/03* (2013.01); *C07K 2319/20* (2013.01)

(58) Field of Classification Search
CPC ............. C07K 14/7051; C07K 14/465; C07K 2319/00; C07K 2319/03; C07K 2319/20; C12N 15/85; C12N 15/63; C07H 2/041
See application file for complete search history.

(56) References Cited

U.S. PATENT DOCUMENTS

| | | |
|---|---|---|
| 5,199,942 A | 4/1993 | Gillis |
| 5,350,674 A | 9/1994 | Boenisch et al. |
| 5,399,346 A | 3/1995 | Anderson et al. |
| 5,580,859 A | 12/1996 | Felgner et al. |
| 5,585,362 A | 12/1996 | Wilson et al. |
| 5,589,466 A | 12/1996 | Felgner et al. |
| 5,858,358 A | 1/1999 | June et al. |
| 5,883,223 A | 3/1999 | Gray |
| 5,993,434 A | 11/1999 | Dev et al. |
| 6,181,964 B1 | 1/2001 | Hofmann et al. |
| 6,233,482 B1 | 5/2001 | Hofmann et al. |
| 6,241,701 B1 | 6/2001 | Hofmann |
| 6,326,193 B1 | 12/2001 | Liu et al. |
| 6,352,694 B1 | 3/2002 | June et al. |
| 6,516,223 B2 | 2/2003 | Hofmann |
| 6,534,055 B1 | 3/2003 | June et al. |
| 6,567,694 B2 | 5/2003 | Hayakawa |
| 6,678,556 B1 | 1/2004 | Nolan et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,144,575 B2 | 12/2006 | June et al. |
| 7,171,264 B1 | 1/2007 | Hofmann et al. |
| 7,172,869 B2 | 2/2007 | June et al. |

(Continued)

FOREIGN PATENT DOCUMENTS

| | | |
|---|---|---|
| WO | WO96/23814 | 8/1996 |
| WO | WO01/29058 | 4/2001 |
| WO | WO01/96584 | 12/2001 |

OTHER PUBLICATIONS

Hege et al., Systemic T Cell-independent Tumor Immunity after Transplantation of Universal Receptor—modified Bone Marrow into SCID Mice. J. Exp. Med. 184:2261-2269, 1996.*

Airenne et al, "Recombinant avidin and avidin-fusion proteins." Biomolecular Engineering, 16:87-92, 1999.

Ang et al., "Generating a Chimeric Antigen Receptor to Redirect T-Cell Specificity after Infusion." ASGCT abstracts #353, May 18-21, 2011.

Bergan et al., "Development and in vitro validation of anti-mesothelin biobodies that prevent CA125/Mesothelin-dependent cell attachment." 2007, Cancer Lett. 255:263-274 (Abstract).

(Continued)

*Primary Examiner* — Ruixiang Li
(74) *Attorney, Agent, or Firm* — Saul Ewing LLP; Kathryn Doyle

(57) ABSTRACT

The invention provides compositions and methods for adoptive T cell therapy in treating a variety of disorders including cancer, infections, and autoimmune disorders. In one embodiment, the invention provides a universal immune receptor (UnivIR) that comprises an extracellular label binding domain, a transmembrane domain, and a cytoplasmic domain or otherwise an intracellular domain.

6 Claims, 14 Drawing Sheets

(56) References Cited

U.S. PATENT DOCUMENTS

| | | | |
|---|---|---|---|
| 7,173,116 B2 | 2/2007 | Fewell et al. | |
| 7,175,843 B2 | 2/2007 | June et al. | |
| 7,232,566 B2 | 6/2007 | June et al. | |
| 2002/0111474 A1 | 8/2002 | Capon et al. | |
| 2004/0059285 A1 | 3/2004 | Mathiesen et al. | |
| 2004/0092907 A1 | 5/2004 | Mathiesen et al. | |
| 2004/0101519 A1 | 5/2004 | June et al. | |
| 2005/0052630 A1 | 3/2005 | Smith et al. | |
| 2005/0070841 A1 | 3/2005 | Mathiesen et al. | |
| 2006/0034810 A1 | 2/2006 | Riley et al. | |
| 2006/0121005 A1 | 6/2006 | Berenson et al. | |
| 2007/0128708 A1 | 6/2007 | Gamelin | |
| 2009/0011984 A1* | 1/2009 | Yla-Herttuala .. | A61K 47/48146 514/19.1 |
| 2013/0287752 A1* | 10/2013 | Davila ............... | C07K 16/2863 424/93.71 |

OTHER PUBLICATIONS

Berge et al., "Selective Expansion of a Peripheral Blood CD8+ Memory T Cell Subset Expressing Both Granzyme B and L-Selectin During Primary Viral Infection in Renal Allograft Recipients." 1998, Transplant Proc. 30(8):3975-3977.

Bierer et al., "Cyclosporin A and FK506: molecular mechanisms of immunosuppression and probes for transplantation biology." Curr. Opin. Immun. 5:763-773, 1993.

Bird et al., "Single-chain antigen-binding proteins." 1988, Science 242:423-426.

Cougot, et al., "'Cap-tabolism'." 2001, Trends in Biochem. Sci., 29:436-444 (Abstract).

Elango, et al., "Optimized transfection of mRNA transcribed from a d(A/T)100 tail-containing vector." 2005, Biochim. Biophys. Res. Commun., 330:958-966 (Abstract).

Ertl et al, "Considerations for the clinical application of chimeric antigen receptor T cells: observations from a recombinant DNA Advisory Committee Symposium held Jun. 15, 2010." 2011, Cancer Res, 71:3175-81.

Eshhar et al., "Specific activation and targeting of cytotoxic lymphocytes through chimeric single chains consisting of antibody-binding domains and the gamma or zeta subunits of the immunoglobulin and T-cell receptors." 1993, Proc Natl Acad Sci U S A 90(2):720-724.

Garland et al., "The use of Teflon cell culture bags to expand functionally active CD8+ cytotoxic T lymphocytes." 1999, J. Immunol Meth. 227(1-2):53-63.

Ghosh et al.,"Design of liposomes for circumventing the reticuloendothelial cells." 1991 Glycobiology 5: 505-10 (Abstract).

Green et al., "The properties of subunits of avidin coupled to sepharose." 1973, Biochem. J. 133:687-700.

Haanen et al., "Selective Expansion of Cross-reactive CD8+ Memory T Cells by Viral Variants." 1999, J. Exp. Med. 190(9):1319-1328.

Henderson et al., "Comparison of the effects of FK-506, cyclosporin A and rapamycin on IL-2 production." 1991, Immun. 73:316-321.

Huston et al., "Protein engineering of antibody binding sites: Recovery of specific activity in an anti-digoxin single-chain Fv analogue produced in *Escherichia coli*", 1988, Proc. Natl. Acad. Sci. USA 85:5879-5883.

International Search Report for PCT/US12/56901 dated Feb. 12, 2013.

Johnson et al., "Gene Transfer of Tumor-Reactive TCR Confers Both High Avidity and Tumor Reactivity to Nonreactive Peripheral Blood Mononuclear Cells and Tumor-Infiltrating Lymphocytes1" 2006, J. Immunol 177:6548-6559.

Junghans, "Strategy escalation: an emerging paradigm for safe clinical development of T cell gene therapies." 2010, Journal of Translational Medicine, 8:55.

Kochenderfer et al., "Eradication of B-lineage cells and regression of lymphoma in a patient treated with autologous T cells genetically engineered to recognize CD19." 2010, Blood 116:4099-4120.

Koehler et al., "CD28 costimulation overcomes transforming growth factor-beta-mediated repression of proliferation of redirected human CD4+ and CD8+ T cells in an antitumor cell attack." 2007, Cancer Res. 67:2265-2273.

Kohn et al., "CARs on track in the clinic." 2011, Mol. Ther. 19:432-438.

Laitinen et al., "Biotin induces tetramerization of a recombinant monomeric avidin. A model for protein-protein interactions." 2001, J. Biol. Chem. 276:8219-8224.

Lanitis et al., "Redirected antitumor activity of primary human lymphocytes transduced with a fully human anti-mesothelin chimeric receptor." 2012, Mol. Ther. 20:633-643.

Liu et al., "Calcineurin Is a Common Target of Cyclophilin-Cyclosporin A and FKBP-FK506 Complexes" Cell 66:807-815, 1991.

Nacheva and Berzal-Herranz, "Preventing nondesired RNA-primed RNA extension catalyzed by T7 RNA polymerase", Eur. J. Biochem., 270:1485-65 (2003).

Nishikawa, et al., "Nonviral vectors in the new millennium: delivery barriers in gene transfer", Hum. Gene Ther., 12(8):861-70 (2001) (Abstract).

Paganelli et al., "Three-step monoclonal antibody tumor targeting in carcinoembryonic antigen-positive patients." 1991, Cancer Res. 51:5960-5966.

Perez et al., "Suppression of HIV-1 infection in primary CD4 T cells transduced with a self-inactivating lentiviral vector encoding a membrane expressed gp41-derived fusion inhibitor." 2005, Clin. Immunol. 115:26-32 (Abstract).

Porter et al., "Chimeric antigen receptor-modified T cells in chronic lymphoid leukemia." 2011 N. Engl. J. Med. 365(8):725-33.

Rosenberg et al., "Personalized cell transfer immunotherapy for B-cell malignancies and solid cancers." 2011, Mol. Ther. 19:1928-1930.

Rosenberg et al., "Use of tumor-infiltrating lymphocytes and interleukin-2 in the immunotherapy of patients with metastatic melanoma. A preliminary report." New Eng. J. of Med. 319:1676, 1988.

Salomon et al., "Complexities of CD28/B7: CTLA-4 costimulatory pathways in autoimmunity and transplantation." 2001, Annu. Rev. Immunol. 19:225-252 (Abstract).

Samuel et al., "Detection of prosthetic vascular graft infection using avidin/indium-111-biotin scintigraphy." 1996, J. Nucl. Med 37:55-61.

Schenborn and Mierendorf, "A novel transcription property of SP6 and T7 RNA polymerases: dependence on template structure." Nuc Acids Res., 13:6223-36 (1985).

Scholler et al., "Method for generation of in vivo biotinylated recombinant antibodies by yeast mating." 2006, J. Immnol. Methods 317:132-143.

Song et al., "In vivo persistence, tumor localization, and antitumor activity of CAR-engineered T cells is enhanced by costimulatory signaling through CD137 (4-1BB)." 2011, Cancer Res. 71:4617-4627.

Stepinski, et al., "Synthesis and properties of mRNAs containing the novel "anti-reverse" cap analogs 7-methyl(3'-0-methyl)GpppG and 7-methyl(3'-deoxy)GpppG", RNA, 7:1468-95 (2001).

Stratton et al., "Plasma concentration of 3-hydroxyisovaleryl carnitine is an early and sensitive indicator of marginal biotin deficiency in humans." 2010, Am. J. Clin. Nutr. 92:1399-1405.

Ui-Tei et al., "Sensitive assay of RNA interference in *Drosophila* and Chinese hamster cultured cells using firefly luciferase gene as target." 2000 FEBS Letters 479: 79-82.

\* cited by examiner

SEQUENCE LISTING

<160> NUMBER OF SEQ ID NOS: 34

<210> SEQ ID NO 1
<211> LENGTH: 15
<212> TYPE: DNA
<213> ORGANISM: Artificial sequence
<220> FEATURE:
<223> OTHER INFORMATION: Chemically synthesized

<400> SEQUENCE: 1
aaaagcctag gatcc                                                    15

<210> SEQ ID NO 2
<211> LENGTH: 15
<212> TYPE: DNA
<213> ORGANISM: Artificial sequence
<220> FEATURE:
<223> OTHER INFORMATION: Chemically synthesized

<400> SEQUENCE: 2
aaccgcgcta gcaaa                                                    15

<210> SEQ ID NO 3
<211> LENGTH: 23
<212> TYPE: DNA
<213> ORGANISM: Artificial sequence
<220> FEATURE:
<223> OTHER INFORMATION: Chemically synthesized

<400> SEQUENCE: 3
aaaggatccg ctagaaagag aac                                           23

<210> SEQ ID NO 4
<211> LENGTH: 23
<212> TYPE: DNA
<213> ORGANISM: Artificial sequence
<220> FEATURE:
<223> OTHER INFORMATION: Chemically synthesized

<400> SEQUENCE: 4
aaagctagcc tcggagaact tcc                                              23

<210> SEQ ID NO 5
<211> LENGTH: 463
<212> TYPE: PRT
<213> ORGANISM: Artificial sequence
<220> FEATURE:
<223> OTHER INFORMATION: Chemically synthesized

<400> SEQUENCE: 5

Met Ala Leu Pro Val Thr Ala Leu Leu Leu Pro Leu Ala Leu Leu Leu
1               5                   10                  15

His Ala Ala Arg Pro Gly Ser Ala Arg Lys Arg Thr Gln Pro Thr Phe
            20                  25                  30

Gly Phe Thr Val Asn Trp Lys Phe Ser Glu Ser Thr Thr Val Phe Thr
        35                  40                  45

Gly Gln Cys Phe Ile Asp Arg Asn Gly Lys Glu Val Leu Lys Thr Met
    50                  55                  60

Trp Leu Leu Ile Asn Ile Phe Thr Arg Leu Arg Thr Gln Lys Glu Gly
65                  70                  75                  80

Gly Ser Gly Gly Ser Ala Arg Lys Cys Ser Leu Thr Gly Lys Trp Thr
                85                  90                  95

Asn Asp Leu Gly Ser Asn Met Thr Ile Gly Ala Val Asn Ser Arg Gly
            100                 105                 110

Glu Phe Thr Gly Thr Tyr Ile Thr Ala Val Thr Ala Thr Ser Asn Glu
        115                 120                 125

Ile Lys Glu Ser Pro Leu His Gly Thr Gln Asn Thr Ile Asn Lys Ser
    130                 135                 140

Gly Gly Ser Thr Thr Val Phe Thr Gly Gln Cys Phe Ile Asp Arg Asn
145                 150                 155                 160

Gly Lys Glu Val Leu Lys Thr Met Trp Leu Leu Arg Ser Ser Val Asn
                165                 170                 175

Asp Ile Gly Asp Asp Trp Lys Ala Thr Arg Val Gly Ile Asn Ile Phe
            180                 185                 190

Thr Arg Leu Arg Thr Gln Lys Glu Gly Gly Ser Gly Gly Ser Ala Arg
        195                 200                 205

Lys Cys Ser Leu Thr Gly Lys Trp Thr Asn Asp Leu Gly Ser Asn Met
    210                 215                 220

Thr Ile Gly Ala Val Asn Ser Arg Gly Glu Phe Thr Gly Thr Tyr Ile
225                 230                 235                 240

Thr Ala Val Thr Ala Thr Ser Asn Glu Ile Lys Glu Ser Pro Leu His
                245                 250                 255

Gly Thr Gln Asn Thr Ile Asn Lys Arg Thr Gln Pro Thr Phe Gly Phe
            260                 265                 270

Thr Val Asn Trp Lys Phe Ser Glu Ala Ser Thr Thr Pro Ala Pro
        275                 280                 285

Arg Pro Pro Thr Pro Ala Pro Thr Ile Ala Ser Gln Pro Leu Ser Leu
    290                 295                 300

```
Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 6
<211> LENGTH: 526
<212> TYPE: PRT
<213> ORGANISM: Artificial sequence
<220> FEATURE:
<223> OTHER INFORMATION: Chemically synthesized

<400> SEQUENCE: 6

Met Ala Leu Pro Val Thr Ala Leu Leu Leu Pro Leu Ala Leu Leu Leu
1               5                   10                  15

His Ala Ala Arg Pro Gly Ser Ala Arg Lys Arg Thr Gln Pro Thr Phe
                20                  25                  30

Gly Phe Thr Val Asn Trp Lys Phe Ser Glu Ser Thr Thr Val Phe Thr
            35                  40                  45

Gly Gln Cys Phe Ile Asp Arg Asn Gly Lys Glu Val Leu Lys Thr Met
        50                  55                  60

Trp Leu Leu Arg Ser Ser Val Asn Asp Ile Gly Asp Asp Trp Lys Ala
65                  70                  75                  80

Thr Arg Val Gly Ile Asn Ile Phe Thr Arg Leu Arg Thr Gln Lys Glu
                85                  90                  95

Gly Gly Ser Gly Gly Ser Ala Arg Lys Cys Ser Leu Thr Gly Lys Trp
            100                 105                 110

Thr Asn Asp Leu Gly Ser Asn Met Thr Ile Gly Ala Val Asn Ser Arg
        115                 120                 125

Gly Glu Phe Thr Gly Thr Tyr Ile Thr Ala Val Thr Ala Thr Ser Asn
    130                 135                 140

Glu Ile Lys Glu Ser Pro Leu His Gly Thr Gln Asn Thr Ile Asn Lys
145                 150                 155                 160

Ser Gly Gly Ser Thr Thr Val Phe Thr Gly Gln Cys Phe Ile Asp Arg
                165                 170                 175

Asn Gly Lys Glu Val Leu Lys Thr Met Trp Leu Leu Arg Ser Ser Val
            180                 185                 190

Asn Asp Ile Gly Asp Asp Trp Lys Ala Thr Arg Val Gly Ile Asn Ile
        195                 200                 205
```

Phe Thr Arg Leu Arg Thr Gln Lys Glu Gly Ser Gly Gly Ser Ala
    210                 215                 220

Arg Lys Cys Ser Leu Thr Gly Lys Trp Thr Asn Asp Leu Gly Ser Asn
225                 230                 235                 240

Met Thr Ile Gly Ala Val Asn Ser Arg Gly Glu Phe Thr Gly Thr Tyr
                245                 250                 255

Ile Thr Ala Val Thr Ala Thr Ser Asn Glu Ile Lys Glu Ser Pro Leu
                260                 265                 270

His Gly Thr Gln Asn Thr Ile Asn Lys Arg Thr Gln Pro Thr Phe Gly
                275                 280                 285

Phe Thr Val Asn Trp Lys Phe Ser Glu Ala Ser Thr Thr Thr Pro Ala
            290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Phe Trp Val Leu Val Val Val Gly
                340                 345                 350

Gly Val Leu Ala Cys Tyr Ser Leu Leu Val Thr Val Ala Phe Ile Ile
            355                 360                 365

Phe Trp Val Arg Ser Lys Arg Ser Arg Leu Leu His Ser Asp Tyr Met
            370                 375                 380

Asn Met Thr Pro Arg Arg Pro Gly Pro Thr Arg Lys His Tyr Gln Pro
385                 390                 395                 400

Tyr Ala Pro Pro Arg Asp Phe Ala Ala Tyr Arg Ser Ile Asp Arg Val
                405                 410                 415

Lys Phe Ser Arg Ser Ala Asp Ala Pro Ala Tyr Gln Gln Gly Gln Asn
                420                 425                 430

Gln Leu Tyr Asn Glu Leu Asn Leu Gly Arg Arg Glu Glu Tyr Asp Val
            435                 440                 445

Leu Asp Lys Arg Arg Gly Arg Asp Pro Glu Met Gly Gly Lys Pro Arg
        450                 455                 460

Arg Lys Asn Pro Gln Glu Gly Leu Tyr Asn Glu Leu Gln Lys Asp Lys
465                 470                 475                 480

Met Ala Glu Ala Tyr Ser Glu Ile Gly Met Lys Gly Glu Arg Arg Arg
                485                 490                 495

Gly Lys Gly His Asp Gly Leu Tyr Gln Gly Leu Ser Thr Ala Thr Lys
            500                 505                 510

Asp Thr Tyr Asp Ala Leu His Met Gln Ala Leu Pro Pro Arg
        515                 520                 525

<210> SEQ ID NO 7
<211> LENGTH: 522
<212> TYPE: PRT
<213> ORGANISM: Artificial sequence
<220> FEATURE:
<223> OTHER INFORMATION: Chemically synthesized

<400> SEQUENCE: 7

Met Ala Leu Pro Val Thr Ala Leu Leu Leu Pro Leu Ala Leu Leu Leu
1               5                   10                  15

His Ala Ala Arg Pro Gly Ser Ala Arg Lys Arg Thr Gln Pro Thr Phe
            20                  25                  30

Gly Phe Thr Val Asn Trp Lys Phe Ser Glu Ser Thr Thr Val Phe Thr
        35                  40                  45

```
Gly Gln Cys Phe Ile Asp Arg Asn Gly Lys Glu Val Leu Lys Thr Met
    50                  55                  60

Trp Leu Leu Arg Ser Ser Val Asn Asp Ile Gly Asp Asp Trp Lys Ala
65                  70                  75                  80

Thr Arg Val Gly Ile Asn Ile Phe Thr Arg Leu Arg Thr Gln Lys Glu
                    85                  90                  95

Gly Gly Ser Gly Gly Ser Ala Arg Lys Cys Ser Leu Thr Gly Lys Trp
                100                 105                 110

Thr Asn Asp Leu Gly Ser Asn Met Thr Ile Gly Ala Val Asn Ser Arg
            115                 120                 125

Gly Glu Phe Thr Gly Thr Tyr Ile Thr Ala Val Thr Ala Thr Ser Asn
    130                 135                 140

Glu Ile Lys Glu Ser Pro Leu His Gly Thr Gln Asn Thr Ile Asn Lys
145                 150                 155                 160

Ser Gly Gly Ser Thr Thr Val Phe Thr Gly Gln Cys Phe Ile Asp Arg
                165                 170                 175

Asn Gly Lys Glu Val Leu Lys Thr Met Trp Leu Leu Arg Ser Ser Val
                180                 185                 190

Asn Asp Ile Gly Asp Asp Trp Lys Ala Thr Arg Val Gly Ile Asn Ile
    195                 200                 205

Phe Thr Arg Leu Arg Thr Gln Lys Glu Gly Gly Ser Gly Gly Ser Ala
    210                 215                 220

Arg Lys Cys Ser Leu Thr Gly Lys Trp Thr Asn Asp Leu Gly Ser Asn
225                 230                 235                 240

Met Thr Ile Gly Ala Val Asn Ser Arg Gly Glu Phe Thr Gly Thr Tyr
                245                 250                 255

Ile Thr Ala Val Thr Ala Thr Ser Asn Glu Ile Lys Glu Ser Pro Leu
            260                 265                 270

His Gly Thr Gln Asn Thr Ile Asn Lys Arg Thr Gln Pro Thr Phe Gly
    275                 280                 285

Phe Thr Val Asn Trp Lys Phe Ser Glu Ala Ser Thr Thr Thr Pro Ala
    290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Ile Tyr Ile Trp Ala Pro Leu Ala
            340                 345                 350

Gly Thr Cys Gly Val Leu Leu Leu Ser Leu Val Ile Thr Leu Tyr Cys
    355                 360                 365

Lys Arg Gly Arg Lys Lys Leu Leu Tyr Ile Phe Lys Gln Pro Phe Met
    370                 375                 380

Arg Pro Val Gln Thr Thr Gln Glu Glu Asp Gly Cys Ser Cys Arg Phe
385                 390                 395                 400

Pro Glu Glu Glu Glu Gly Gly Cys Glu Leu Arg Val Lys Phe Ser Arg
                405                 410                 415

Ser Ala Asp Ala Pro Ala Tyr Gln Gln Gly Gln Asn Gln Leu Tyr Asn
            420                 425                 430

Glu Leu Asn Leu Gly Arg Arg Glu Glu Tyr Asp Val Leu Asp Lys Arg
    435                 440                 445

Arg Gly Arg Asp Pro Glu Met Gly Gly Lys Pro Arg Arg Lys Asn Pro
    450                 455                 460
```

```
Gln Glu Gly Leu Tyr Asn Glu Leu Gln Lys Asp Lys Met Ala Glu Ala
465                 470                 475                 480

Tyr Ser Glu Ile Gly Met Lys Gly Glu Arg Arg Gly Lys Gly His
                485                 490                 495

Asp Gly Leu Tyr Gln Gly Leu Ser Thr Ala Thr Lys Asp Thr Tyr Asp
            500                 505                 510

Ala Leu His Met Gln Ala Leu Pro Pro Arg
            515                 520

<210> SEQ ID NO 8
<211> LENGTH: 404
<212> TYPE: PRT
<213> ORGANISM: Artificial sequence
<220> FEATURE:
<223> OTHER INFORMATION: Chemically synthesized

<400> SEQUENCE: 8

Met Ala Leu Pro Val Thr Ala Leu Leu Leu Pro Leu Ala Leu Leu Leu
1               5                   10                  15

His Ala Ala Arg Pro Gly Ser Met Val His Ala Thr Ser Pro Leu Leu
                20                  25                  30

Leu Leu Leu Leu Leu Ser Leu Ala Leu Val Ala Pro Gly Leu Ser Ala
            35                  40                  45

Arg Lys Cys Ser Leu Thr Gly Lys Trp Thr Asn Asp Leu Gly Ser Asn
50                  55                  60

Met Thr Ile Gly Ala Val Asn Ser Arg Gly Glu Phe Thr Gly Thr Tyr
65                  70                  75                  80

Ile Thr Ala Val Thr Ala Thr Ser Asn Glu Ile Lys Glu Ser Pro Leu
                85                  90                  95

His Gly Thr Gln Asn Thr Ile Asn Lys Arg Thr Gln Pro Thr Phe Gly
            100                 105                 110

Phe Thr Val Asn Trp Lys Phe Ser Glu Ser Thr Thr Val Phe Thr Gly
        115                 120                 125

Gln Cys Phe Ile Asp Arg Asn Gly Lys Glu Val Leu Lys Thr Met Trp
130                 135                 140

Leu Leu Arg Ser Ser Val Asn Asp Ile Gly Asp Asp Trp Lys Ala Thr
145                 150                 155                 160

Arg Val Gly Ile Asn Ile Phe Thr Arg Leu Arg Thr Gln Lys Glu Ala
                165                 170                 175

Ser Thr Thr Thr Pro Ala Pro Arg Pro Pro Thr Pro Ala Pro Thr Ile
            180                 185                 190

Ala Ser Gln Pro Leu Ser Leu Arg Pro Glu Ala Cys Arg Pro Ala Ala
        195                 200                 205

Gly Gly Ala Val His Thr Arg Gly Leu Asp Phe Ala Cys Asp Phe Trp
210                 215                 220

Val Leu Val Val Gly Gly Val Leu Ala Cys Tyr Ser Leu Leu Val
225                 230                 235                 240

Thr Val Ala Phe Ile Ile Phe Trp Val Arg Ser Lys Arg Ser Arg Leu
                245                 250                 255

Leu His Ser Asp Tyr Met Asn Met Thr Pro Arg Arg Pro Gly Pro Thr
            260                 265                 270

Arg Lys His Tyr Gln Pro Tyr Ala Pro Pro Arg Asp Phe Ala Ala Tyr
        275                 280                 285

Arg Ser Ile Asp Arg Val Lys Phe Ser Arg Ser Ala Asp Ala Pro Ala
290                 295                 300
```

-continued

```
Tyr Gln Gln Gly Gln Asn Gln Leu Tyr Asn Glu Leu Asn Leu Gly Arg
305                 310                 315                 320

Arg Glu Glu Tyr Asp Val Leu Asp Lys Arg Arg Gly Arg Asp Pro Glu
            325                 330                 335

Met Gly Gly Lys Pro Arg Arg Lys Asn Pro Gln Glu Gly Leu Tyr Asn
        340                 345                 350

Glu Leu Gln Lys Asp Lys Met Ala Glu Ala Tyr Ser Glu Ile Gly Met
    355                 360                 365

Lys Gly Glu Arg Arg Arg Gly Lys Gly His Asp Gly Leu Tyr Gln Gly
370                 375                 380

Leu Ser Thr Ala Thr Lys Asp Thr Tyr Asp Ala Leu His Met Gln Ala
385                 390                 395                 400

Leu Pro Pro Arg

<210> SEQ ID NO 9
<211> LENGTH: 358
<212> TYPE: PRT
<213> ORGANISM: Artificial sequence
<220> FEATURE:
<223> OTHER INFORMATION: Chemically synthesized

<400> SEQUENCE: 9

Met Ala Leu Pro Val Thr Ala Leu Leu Leu Pro Leu Ala Leu Leu Leu
1               5                   10                  15

His Ala Ala Arg Pro Gly Ser Met Val His Ala Thr Ser Pro Leu Leu
            20                  25                  30

Leu Leu Leu Leu Leu Ser Leu Ala Leu Val Ala Pro Gly Leu Ser Ala
        35                  40                  45

Arg Lys Cys Ser Leu Thr Gly Lys Trp Thr Asn Asp Leu Gly Ser Asn
50                  55                  60

Met Thr Ile Gly Ala Val Asn Ser Arg Gly Glu Phe Thr Gly Thr Tyr
65                  70                  75                  80

Ile Thr Ala Val Thr Ala Thr Ser Asn Glu Ile Lys Glu Ser Pro Leu
                85                  90                  95

His Gly Thr Gln Asn Thr Ile Asn Lys Arg Thr Gln Pro Thr Phe Gly
            100                 105                 110

Phe Thr Val Asn Trp Lys Phe Ser Glu Ser Thr Thr Val Phe Thr Gly
        115                 120                 125

Gln Cys Phe Ile Asp Arg Asn Gly Lys Glu Val Leu Lys Thr Met Trp
    130                 135                 140

Leu Leu Arg Ser Ser Val Asn Asp Ile Gly Asp Asp Trp Lys Ala Thr
145                 150                 155                 160

Arg Val Gly Ile Asn Ile Phe Thr Arg Leu Arg Thr Gln Lys Glu Ala
                165                 170                 175

Ser Thr Thr Thr Pro Ala Pro Arg Pro Pro Thr Pro Ala Pro Thr Ile
            180                 185                 190

Ala Ser Gln Pro Leu Ser Leu Arg Pro Glu Ala Cys Arg Pro Ala Ala
        195                 200                 205

Gly Gly Ala Val His Thr Arg Gly Leu Asp Phe Ala Cys Asp Ile Tyr
    210                 215                 220

Ile Trp Ala Pro Leu Ala Gly Thr Cys Gly Val Leu Leu Leu Ser Leu
225                 230                 235                 240

Val Ile Thr Leu Tyr Cys Arg Val Lys Phe Ser Arg Ser Ala Asp Ala
                245                 250                 255

Pro Ala Tyr Gln Gln Gly Gln Asn Gln Leu Tyr Asn Glu Leu Asn Leu
```

```
                    260                 265                 270
Gly Arg Arg Glu Glu Tyr Asp Val Leu Asp Lys Arg Arg Gly Arg Asp
                275                 280                 285

Pro Glu Met Gly Gly Lys Pro Arg Arg Lys Asn Pro Gln Glu Gly Leu
        290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
                325                 330                 335

Gln Gly Leu Ser Thr Ala Thr Lys Asp Thr Tyr Asp Ala Leu His Met
                340                 345                 350

Gln Ala Leu Pro Pro Arg
                355

<210> SEQ ID NO 10
<211> LENGTH: 400
<212> TYPE: PRT
<213> ORGANISM: Artificial sequence
<220> FEATURE:
<223> OTHER INFORMATION: Chemically synthesized

<400> SEQUENCE: 10

Met Ala Leu Pro Val Thr Ala Leu Leu Leu Pro Leu Ala Leu Leu Leu
1               5                   10                  15

His Ala Ala Arg Pro Gly Ser Met Val His Ala Thr Ser Pro Leu Leu
                20                  25                  30

Leu Leu Leu Leu Leu Ser Leu Ala Leu Val Ala Pro Gly Leu Ser Ala
            35                  40                  45

Arg Lys Cys Ser Leu Thr Gly Lys Trp Thr Asn Asp Leu Gly Ser Asn
50                  55                  60

Met Thr Ile Gly Ala Val Asn Ser Arg Gly Glu Phe Thr Gly Thr Tyr
65                  70                  75                  80

Ile Thr Ala Val Thr Ala Thr Ser Asn Glu Ile Lys Glu Ser Pro Leu
                85                  90                  95

His Gly Thr Gln Asn Thr Ile Asn Lys Arg Thr Gln Pro Thr Phe Gly
                100                 105                 110

Phe Thr Val Asn Trp Lys Phe Ser Glu Ser Thr Thr Val Phe Thr Gly
            115                 120                 125

Gln Cys Phe Ile Asp Arg Asn Gly Lys Glu Val Leu Lys Thr Met Trp
        130                 135                 140

Leu Leu Arg Ser Ser Val Asn Asp Ile Gly Asp Asp Trp Lys Ala Thr
145                 150                 155                 160

Arg Val Gly Ile Asn Ile Phe Thr Arg Leu Arg Thr Gln Lys Glu Ala
                165                 170                 175

Ser Thr Thr Thr Pro Ala Pro Arg Pro Pro Thr Pro Ala Pro Thr Ile
                180                 185                 190

Ala Ser Gln Pro Leu Ser Leu Arg Pro Glu Ala Cys Arg Pro Ala Ala
            195                 200                 205

Gly Gly Ala Val His Thr Arg Gly Leu Asp Phe Ala Cys Asp Ile Tyr
        210                 215                 220

Ile Trp Ala Pro Leu Ala Gly Thr Cys Gly Val Leu Leu Leu Ser Leu
225                 230                 235                 240

Val Ile Thr Leu Tyr Cys Lys Arg Gly Arg Lys Lys Leu Leu Tyr Ile
                245                 250                 255

Phe Lys Gln Pro Phe Met Arg Pro Val Gln Thr Thr Gln Glu Glu Asp
```

```
            260                 265                 270
Gly Cys Ser Cys Arg Phe Pro Glu Glu Glu Gly Gly Cys Glu Leu
            275                 280                 285

Arg Val Lys Phe Ser Arg Ser Ala Asp Ala Pro Ala Tyr Gln Gln Gly
            290                 295                 300

Gln Asn Gln Leu Tyr Asn Glu Leu Asn Leu Gly Arg Arg Glu Glu Tyr
305                 310                 315                 320

Asp Val Leu Asp Lys Arg Arg Gly Arg Asp Pro Glu Met Gly Gly Lys
                325                 330                 335

Pro Arg Arg Lys Asn Pro Gln Glu Gly Leu Tyr Asn Glu Leu Gln Lys
                340                 345                 350

Asp Lys Met Ala Glu Ala Tyr Ser Glu Ile Gly Met Lys Gly Glu Arg
                355                 360                 365

Arg Arg Gly Lys Gly His Asp Gly Leu Tyr Gln Gly Leu Ser Thr Ala
                370                 375                 380

Thr Lys Asp Thr Tyr Asp Ala Leu His Met Gln Ala Leu Pro Pro Arg
385                 390                 395                 400
```

<210> SEQ ID NO 11
<211> LENGTH: 1443
<212> TYPE: DNA
<213> ORGANISM: Artificial sequence
<220> FEATURE:
<223> OTHER INFORMATION: Chemically synthesized

<400> SEQUENCE: 11

```
atggccttac cagtgaccgc cttgctcctg ccgctggcct tgctgctcca cgccgccagg      60
ccgggatccg ctagaaagag aacccagccc acattcggct tcaccgtgaa ctggaagttc     120
agcgagagca ccaccgtgtt caccggccag tgcttcatcg accggaacgg caaagaggtg     180
ctgaaaacca tgtggctgct gcggagcagc gtgaacgaca tcggcgacga ctggaaggcc     240
accagagtgg gcatcaacat cttcacccgg ctgcggaccc agaaagaggg aggctctgga     300
ggctccgcca gaaagtgtag cctgacaggc aagtggacca acgacctggg cagcaacatg     360
accatcggcg ccgtgaacag cagaggcgag ttcaccggca cctacatcac cgccgtgacc     420
gccaccagca acgagatcaa agagagcccc ctgcacggca cccagaacac catcaacaag     480
agcggcggct ccaccacagt gtttacagga cagtgtttta tcgaccgcaa tgggaaagaa     540
gtcctcaaga caatgtggct cctgagaagc tccgtgaatg atatcgggga tgattggaaa     600
gccacacgcg tgggaatcaa tatctttacc agactccgca cagaaagaag gcggaagc      660
ggcggcagcg cccggaagtg ttccctgacc ggaaaatgga caaatgatct ggggtccaat     720
atgacaatcg gggctgtgaa ctctcggggc gagtttacag gcacatatat tacagctgtc     780
accgccacct ctaatgagat caaggaatct cctctgcacg ggacacagaa tactattaac     840
aagcggaccc agcctacctt tgggtttaca gtcaattgga gttctccga ggctagcacc     900
acgacgccag cgccgcgacc accaacaccg gcgcccacca tcgcgtcgca gcccctgtcc     960
ctgcgcccag gaggcgtgcc gccagcggcg gggggcgcag tgcacacgag ggggctggac    1020
ttcgcctgtg atatctacat ctgggcgccc ttgccgggga cttgtggggt ccttctcctg    1080
tcactggtta tcaccctta ctgcagagtg aagttcagca ggagcgcaga cgcccccgcg    1140
taccagcagg gccagaacca gctctataac gagctcaatc taggacgaag agaggagtac    1200
gatgttttgg acaagagacg tggccggac cctgagatgg gggaaagcc gagaaggaag    1260
aaccctcagg aaggcctgta caatgaactg cagaaagata agatggcgga ggcctacagt    1320
```

```
gagattggga tgaaaggcga gcgccggagg ggcaaggggc acgatggcct ttaccagggt   1380
ctcagtacag ccaccaagga cacctacgac gcccttcaca tgcaggccct gcccctcgc    1440 taa                                                                1443

<210> SEQ ID NO 12
<211> LENGTH: 1581
<212> TYPE: DNA
<213> ORGANISM: Artificial sequence
<220> FEATURE:
<223> OTHER INFORMATION: Chemically synthesized

<400> SEQUENCE: 12
atggccttac cagtgaccgc cttgctcctg ccgctggcct tgctgctcca cgccgccagg     60
ccgggatccg ctagaaagag aacccagccc acattcggct tcaccgtgaa ctggaagttc    120
agcgagagca ccaccgtgtt caccggccag tgcttcatcg accggaacgg caagagggtg    180
ctgaaaacca tgtggctgct gcggagcagc gtgaacgaca tcggcgacga ctggaaggcc    240
accagagtgg gcatcaacat cttcacccgg ctgcggaccc agaaagaggg aggctctgga    300
ggctccgcca gaaagtgtag cctgacaggc aagtggacca cgacctggg  cagcaacatg    360 accatcggcg ccgtgaacag cagaggcgag ttcaccggca cctacatcac cgccgtgacc    420
gccaccagca acgagatcaa agagagcccc ctgcacggca cccagaacac catcaacaag    480
agcggcggct ccaccacagt gttt acagga cagtgttttta tcgaccgcaa tgggaaagaa    540
gtcctcaaga caatgtggct cctgagaagc tccgtgaatg atatcgggga tgattggaaa    600
gccacacgcg tgggaatcaa tatctttacc agactccgca cacagaaaga aggcggaagc    660
ggcggcagcg cccggaagtg ttccctgacc ggaaaatgga caatgatct  ggggtccaat    720 atgacaatcg gggctgtgaa ctctcggggc gagtttacag gcacatatat tacagctgtc    780
accgccacct ctaatgagat caaggaatct cctctgcacg ggacacagaa tactattaac    840
aagcggaccc agcctacctt tgggtttaca gtcaattgga agttctccga ggctagcacc    900
acgacgccag cgccgcgacc accaacaccg gcgcccacca tcgcgtcgca gcccctgtcc    960
ctgcgcccag aggcgtgccg gccagcggcg gggggcgcag tgcacacgag ggggctggac    1020
ttcgcctgtg attttgggt  gctggtggtg gttggtggag tcctggcttg ctatagcttg    1080
ctagtaacag tggcctttat tattttctgg gtgaggagta gaggagcag gctcctgcac    1140 agtgactaca tgaacatgac tccccgccgc cccgggccca cccgcaagca ttaccagccc    1200
tatgccccac cacgcgactt cgcagcctat cgctccatcg atagtgaa  gttcagcagg    1260 agcgcagacg cccccgcgta ccagcagggc cagaaccagc tctataacga gctcaatcta    1320
ggacgaagag aggagtacga tgttttggac aagagacgtg gccgggaccc tgagatgggg    1380
ggaaagccga aaggaagaa  ccctcaggaa ggcctgtaca tgaactgca  gaaagataag    1440 atggcggagg cctacagtga gattggatg  aaaggcgagc gccggagggg caaggggcac    1500
gatggccttt accagggtct cagtacagcc accaaggaca cctacgacgc ccttcacatg    1560
caggccctgc cccctcgcta a                                             1581

<210> SEQ ID NO 13
<211> LENGTH: 1569
<212> TYPE: DNA
<213> ORGANISM: Artificial sequence
<220> FEATURE:
<223> OTHER INFORMATION: Chemically synthesized
```

<400> SEQUENCE: 13

```
atggccttac cagtgaccgc cttgctcctg ccgctggcct tgctgctcca cgccgccagg     60
ccgggatccg ctagaaagag aacccagccc acattcggct tcaccgtgaa ctggaagttc    120
agcgagagca ccaccgtgtt caccggccag tgcttcatcg accggaacgg caaagaggtg    180
ctgaaaacca tgtggctgct gcggagcagc gtgaacgaca tcggcgacga ctggaaggcc    240
accagagtgg gcatcaacat cttcacccgg ctgcggaccc agaaagaggg aggctctgga    300
ggctccgcca gaaagtgtag cctgacaggc aagtggacca cgacctgggc agcaacatg     360
accatcggcg ccgtgaacag cagaggcgag ttcaccggca cctacatcac cgccgtgacc    420
gccaccagca acgagatcaa agagagcccc ctgcacggca cccagaacac catcaacaag    480
agcggcggct ccaccacagt gtttacagga cagtgtttta tcgaccgcaa tgggaaagaa    540
gtcctcaaga caatgtggct cctgagaagc tccgtgaatg atatcgggga tgattggaaa    600
gccacacgcg tgggaatcaa tatctttacc agactccgca cacagaaaga aggcggaagc    660
ggcggcagcg cccggaagtg ttccctgacc ggaaaatgga caaatgatct ggggtccaat    720
atgacaatcg gggctgtgaa ctctcggggc gagtttacag gcacatatat tacagctgtc    780
accgccacct ctaatgagat caaggaatct cctctgcacg gaacacagaa tactattaac    840
aagcggaccc agcctacctt tgggtttaca gtcaattgga gttctccga ggctagcacc     900
acgacgccag cgccgcgacc accaacaccg gcgcccacca tcgcgtcgca gccctgtcc     960
ctgcgcccag aggcgtgccg ccagcggcg ggggcgcag tgcacacgag ggggctggac     1020
ttcgcctgtg atatctacat ctgggcgccc ttggccggga cttgtggggt ccttctcctg    1080
tcactggtta tcacccttta ctgcaaacgg ggcagaaaga aactcctgta tatattcaaa    1140
caaccattta tgagaccagt acaaactact caagaggaag atggctgtag ctgccgattt    1200
ccagaagaag aagaaggagg atgtgaactg agagtgaagt tcagcaggag cgcagacgcc    1260
cccgcgtacc agcagggcca gaaccagctc tataacgagc tcaatctagg acgaagagag    1320
gagtacgatg tttttggaca gagacgtggc cgggaccctg agatgggggg aaagccgaga    1380
aggaagaacc ctcaggaagg cctgtacaat gaactgcaga agataagat ggcggaggcc     1440
tacagtgaga ttgggatgaa aggcgagcgc cggaggggca agggcacga tggcctttac    1500
cagggtctca gtacagccac caaggacacc tacgacgccc ttcacatgca ggccctgccc    1560
cctcgctaa                                                           1569
```

<210> SEQ ID NO 14
<211> LENGTH: 1215
<212> TYPE: DNA
<213> ORGANISM: Artificial sequence
<220> FEATURE:
<223> OTHER INFORMATION: Chemically synthesized

<400> SEQUENCE: 14

```
atggccttac cagtgaccgc cttgctcctg ccgctggcct tgctgctcca cgccgccagg     60
ccgggatcca tggtgcatgc gaccagcccg ctgctgctgc tgctgctgct gagcctggcg    120
ctggtggcgc cgggcctgag cgcgcgcaaa tgcagcctga ccgcaaatg gaccaacgat     180
ctgggcagca acatgaccat tggcgcggtg aacagccgcg gcgaatttac cggcacctat    240
attaccgcgg tgaccgcgac cagcaacgaa attaagaaa gcccgctgca tggcacccag     300
aacaccatta caaacgcac ccagccgacc tttggcttta ccgtgaactg gaaatttagc      360
gaaagcacca ccgtgtttac cggccagtgc tttattgatc gcaacggcaa agaagtgctg    420
```

```
aaaaccatgt ggctgctgcg cagcagcgtg aacgatattg gcgatgattg gaaagcgacc      480
cgcgtgggca ttaacatttt tacccgcctg cgcacccaga aagaagctag caccacgacg      540
ccagcgccgc gaccaccaac accggcgccc accatcgcgt cgcagcccct gtccctgcgc      600
ccagaggcgt gccggccagc ggcgggggggc gcagtgcaca cgaggggggct ggacttcgcc     660 tgtgattttt gggtgctggt ggtggttggt ggagtcctgg cttgctatag cttgctagta      720
acagtggcct ttattatttt ctgggtgagg agtaagagga gcaggctcct gcacagtgac      780
tacatgaaca tgactccccg ccgcccggg cccacccgca agcattacca gccctatgcc       840
ccaccacgcg acttcgcagc ctatcgctcc atcgatagag tgaagttcag caggagcgca      900 gacgccccg cgtaccagca gggccagaac cagctctata cgagctcaa tctaggacga        960 agagaggagt acgatgtttt ggacaagaga cgtggccggg accctgagat gggggggaaag    1020 ccgagaagga agaaccctca ggaaggcctg tacaatgaac tgcagaaaga taagatggcg     1080
gaggcctaca gtgagattgg gatgaaaggc gagcgccgga ggggcaaggg gcacgatggc     1140
ctttaccagg gtctcagtac agccaccaag gacacctacg acgcccttca catgcaggcc    1200
ctgccccctc gctaa                                                      1215

<210> SEQ ID NO 15
<211> LENGTH: 1077
<212> TYPE: DNA
<213> ORGANISM: Artificial sequence
<220> FEATURE:
<223> OTHER INFORMATION: Chemically synthesized

<400> SEQUENCE: 15
atggccttac cagtgaccgc cttgctcctg ccgctggcct tgctgctcca cgccgccagg       60
ccgggatcca tggtgcatgc gaccagcccg ctgctgctgc tgctgctgct gagcctggcg     120
ctggtggcgc cgggcctgag cgcgcgcaaa tgcagcctga ccggcaaatg gaccaacgat     180
ctgggcagca acatgaccat ggcgcgcgtg aacagccgcg cgaatttac cggcaccat      240 attaccgcgg tgaccgcgac cagcaacgaa attaaagaaa gcccgctgca tggcacccag    300
aacaccatta acaaacgcac ccagccgacc tttggcttta ccgtgaactg gaaatttagc    360
gaaagcacca ccgtgtttac cggccagtgc tttattgatc gcaacggcaa agaagtgctg    420
aaaaccatgt ggctgctgcg cagcagcgtg aacgatattg gcgatgattg gaaagcgacc    480
cgcgtgggca ttaacatttt tacccgcctg cgcacccaga aagaagctag caccacgacg    540
ccagcgccgc gaccaccaac accggcgccc accatcgcgt cgcagcccct gtccctgcgc    600
ccagaggcgt gccggccagc ggcgggggggc gcagtgcaca cgaggggggct ggacttcgcc   660 tgtgatatct acatctgggc gcccttggcc gggacttgtg ggtccttct cctgtcactg     720 gttatcaccc tttactgcag agtgaagttc agcaggagcg cagacgcccc cgcgtaccag    780
cagggccaga accagctcta taacgagctc aatctaggac gaagagagga gtacgatgtt     840
ttggacaaga cgtggccgg ggaccctgag atgggggaa agccgagaag gaagaacct       900 caggaaggcc tgtacaatga actgcagaaa gataagatgg cggaggccta cagtgagatt    960
gggatgaaag gcgagcgccg gaggggcaag ggcacgatg gcctttacca gggtctcagt  1020
acagccacca aggacaccta cgacgccctt cacatgcagg ccctgccccc tcgctaa      1077

<210> SEQ ID NO 16
<211> LENGTH: 1203
<212> TYPE: DNA
```

<213> ORGANISM: Artificial sequence
<220> FEATURE:
<223> OTHER INFORMATION: Chemically synthesized

<400> SEQUENCE: 16

```
atggccttac cagtgaccgc cttgctcctg ccgctggcct tgctgctcca cgccgccagg    60
ccgggatcca tggtgcatgc gaccagcccg ctgctgctgc tgctgctgct gagcctggcg   120
ctggtggcgc cgggcctgag cgcgcgcaaa tgcagcctga ccggcaaatg gaccaacgat   180
ctgggcagca acatgaccat ggcgcggtg aacagccgcg cgaatttac cggcacctat    240
attaccgcgg tgaccgcgac cagcaacgaa attaaagaaa gccgctgca tggcacccag   300
aacaccatta caaacgcac ccagccgacc tttggcttta ccgtgaactg gaaatttagc    360
gaaagcacca ccgtgtttac cggccagtgc tttattgatc gcaacggcaa agaagtgctg   420
aaaaccatgt ggctgctgcg cagcagcgtg aacgatattg gcgatgattg aaagcgacc    480
cgcgtgggca ttaacatttt tacccgcctg cgcacccaga agaagctag caccacgacg   540
ccagcgccgc gaccaccaac accggcgccc accatcgcgt cgcagcccct gtccctgcgc   600
ccagaggcgt gccggccagc ggcgggggc gcagtgcaca cgaggggct ggacttcgcc     660
tgtgatatct acatctgggc gcccttggcc gggacttgtg gggtccttct cctgtcactg   720
gttatcaccc tttactgcaa cggggcaga agaaactcc tgtatatatt caaacaacca    780
tttatgagac cagtacaaac tactcaagag gaagatggct gtagctgccg atttccagaa   840
gaagaagaag gaggatgtga actgagagtg aagttcagca ggagcgcaga cgcccccgcg   900
taccagcagg gccagaacca gctctataac gagctcaatc taggacgaag agaggagtac   960
gatgttttgg acaagagacg tggccgggac cctgagatgg ggggaaagcc gagaaggaag  1020
aaccctcagg aaggcctgta caatgaactg cagaaagata gatggcggaa ggcctacagt  1080
gagattggga tgaaaggcga gcgccggagg ggcaaggggc acgatggcct ttaccagggt  1140
ctcagtacag ccaccaagga cacctacgac gcccttcaca tgcaggccct gccccctcgc  1200
taa                                                                1203
```

<210> SEQ ID NO 17
<211> LENGTH: 21
<212> TYPE: PRT
<213> ORGANISM: Artificial sequence
<220> FEATURE:
<223> OTHER INFORMATION: Chemically synthesized

<400> SEQUENCE: 17

```
Met Ala Leu Pro Val Thr Ala Leu Leu Leu Pro Leu Ala Leu Leu Leu
1               5                   10                  15
His Ala Ala Arg Pro
            20
```

<210> SEQ ID NO 18
<211> LENGTH: 274
<212> TYPE: PRT
<213> ORGANISM: Artificial sequence
<220> FEATURE:
<223> OTHER INFORMATION: Chemically synthesized

<400> SEQUENCE: 18

```
Ala Arg Lys Arg Thr Gln Pro Thr Phe Gly Phe Thr Val Asn Trp Lys
1               5                   10                  15

Phe Ser Glu Ser Thr Thr Val Phe Thr Gly Gln Cys Phe Ile Asp Arg
            20                  25                  30
```

```
Asn Gly Lys Glu Val Leu Lys Thr Met Trp Leu Leu Arg Ser Ser Val
         35                  40                  45

Asn Asp Ile Gly Asp Asp Trp Lys Ala Thr Arg Val Gly Ile Asn Ile
 50                  55                  60

Phe Thr Arg Leu Arg Thr Gln Lys Glu Gly Ser Gly Gly Ser Ala
 65                  70                  75                  80

Arg Lys Cys Ser Leu Thr Gly Lys Trp Thr Asn Asp Leu Gly Ser Asn
             85                  90                  95

Met Thr Ile Gly Ala Val Asn Ser Arg Gly Glu Phe Thr Gly Thr Tyr
            100                 105                 110

Ile Thr Ala Val Thr Ala Thr Ser Asn Glu Ile Lys Ser Pro Leu
            115                 120                 125

His Gly Thr Gln Asn Thr Ile Asn Lys Ser Gly Gly Ser Thr Thr Val
        130                 135                 140

Phe Thr Gly Gln Cys Phe Ile Asp Arg Asn Gly Lys Glu Val Leu Lys
145                 150                 155                 160

Thr Met Trp Leu Leu Arg Ser Ser Val Asn Asp Ile Gly Asp Asp Trp
            165                 170                 175

Lys Ala Thr Arg Val Gly Ile Asn Ile Phe Thr Arg Leu Arg Thr Gln
        180                 185                 190

Lys Glu Gly Gly Ser Gly Gly Ser Ala Arg Lys Cys Ser Leu Thr Gly
        195                 200                 205

Lys Trp Thr Asn Asp Leu Gly Ser Asn Met Thr Ile Gly Ala Val Asn
        210                 215                 220

Ser Arg Gly Glu Phe Thr Gly Thr Tyr Ile Thr Ala Val Thr Ala Thr
225                 230                 235                 240

Ser Asn Glu Ile Lys Glu Ser Pro Leu His Gly Thr Gln Asn Thr Ile
            245                 250                 255

Asn Lys Arg Thr Gln Pro Thr Phe Gly Phe Thr Val Asn Trp Lys Phe
            260                 265                 270

Ser Glu

<210> SEQ ID NO 19
<211> LENGTH: 45
<212> TYPE: PRT
<213> ORGANISM: Artificial sequence
<220> FEATURE:
<223> OTHER INFORMATION: Chemically synthesized

<400> SEQUENCE: 19

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
         35                  40                  45

<210> SEQ ID NO 20
<211> LENGTH: 24
<212> TYPE: PRT
<213> ORGANISM: Artificial sequence
<220> FEATURE:
<223> OTHER INFORMATION: Chemically synthesized

<400> SEQUENCE: 20

Ile Tyr Ile Trp Ala Pro Leu Ala Gly Thr Cys Gly Val Leu Leu Leu
 1               5                  10                  15
```

```
Ser Leu Val Ile Thr Leu Tyr Cys
            20
```

```
<210> SEQ ID NO 21
<211> LENGTH: 112
<212> TYPE: PRT
<213> ORGANISM: Artificial sequence
<220> FEATURE:
<223> OTHER INFORMATION: Chemically synthesized

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 22
<211> LENGTH: 27
<212> TYPE: PRT
<213> ORGANISM: Artificial sequence
<220> FEATURE:
<223> OTHER INFORMATION: Chemically synthesized

<400> SEQUENCE: 22

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 23
<211> LENGTH: 43
<212> TYPE: PRT
<213> ORGANISM: Artificial sequence
<220> FEATURE:
<223> OTHER INFORMATION: Chemically synthesized

<400> SEQUENCE: 23

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Ile Asp
        35                  40
```

```
<210> SEQ ID NO 24
<211> LENGTH: 42
<212> TYPE: PRT
<213> ORGANISM: Artificial sequence
<220> FEATURE:
<223> OTHER INFORMATION: Chemically synthesized

<400> SEQUENCE: 24
```

Lys Arg Gly Arg Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 25
<211> LENGTH: 152
<212> TYPE: PRT
<213> ORGANISM: Artificial sequence
<220> FEATURE:
<223> OTHER INFORMATION: Chemically synthesized

<400> SEQUENCE: 25

Met Val His Ala Thr Ser Pro Leu Leu Leu Leu Leu Leu Leu Ser Leu
1               5                   10                  15

Ala Leu Val Ala Pro Gly Leu Ser Ala Arg Lys Cys Ser Leu Thr Gly
                20                  25                  30

Lys Trp Thr Asn Asp Leu Gly Ser Asn Met Thr Ile Gly Ala Val Asn
            35                  40                  45

Ser Arg Gly Glu Phe Thr Gly Thr Tyr Ile Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
        130                 135                 140

Thr Arg Leu Arg Thr Gln Lys Glu
145                 150

<210> SEQ ID NO 26
<211> LENGTH: 63
<212> TYPE: DNA
<213> ORGANISM: Artificial sequence
<220> FEATURE:
<223> OTHER INFORMATION: Chemically synthesized

<400> SEQUENCE: 26
atggccttac cagtgaccgc cttgctcctg ccgctggcct tgctgctcca cgccgccagg        60
ccg                                                                     63

<210> SEQ ID NO 27
<211> LENGTH: 822
<212> TYPE: DNA
<213> ORGANISM: Artificial sequence
<220> FEATURE:
<223> OTHER INFORMATION: Chemically synthesized

<400> SEQUENCE: 27
gctagaaaga gaacccagcc cacattcggc ttcaccgtga actggaagtt cagcgagagc        60
accaccgtgt tcaccggcca gtgcttcatc gaccggaacg gcaaagaggt gctgaaaacc       120
atgtggctgc tgcggagcag cgtgaacgac atcggcgacg actggaaggc caccagagtg       180

```
ggcatcaaca tcttcacccg gctgcggacc cagaaagagg gaggctctgg aggctccgcc    240
agaaagtgta gcctgacagg caagtggacc aacgacctgg gcagcaacat gaccatcggc    300
gccgtgaaca gcagaggcga gttcaccggc acctacatca ccgccgtgac cgccaccagc    360
aacgagatca agagagccc cctgcacggc acccagaaca ccatcaacaa gagcggcggc    420
tccaccacag tgtttacagg acagtgtttt atcgaccgca atgggaaaga agtcctcaag    480
acaatgtggc tcctgagaag ctccgtgaat gatatcgggg atgattggaa agccacacgc    540
gtgggaatca atatctttac cagactccgc acacagaaag aaggcggaag cggcggcagc    600
gcccggaagt gttccctgac cggaaaatgg acaaatgatc tggggtccaa tatgacaatc    660
ggggctgtga actctcgggg cgagtttaca ggcacatata ttacagctgt caccgccacc    720
tctaatgaga tcaaggaatc tcctctgcac gggacacaga atactattaa caagcggacc    780
cagcctacct ttgggtttac agtcaattgg aagttctccg ag                       822

<210> SEQ ID NO 28
<211> LENGTH: 135
<212> TYPE: DNA
<213> ORGANISM: Artificial sequence
<220> FEATURE:
<223> OTHER INFORMATION: Chemically synthesized

<400> SEQUENCE: 28
accacgacgc cagcgccgcg accaccaaca ccggcgccca ccatcgcgtc gcagcccctg     60
tccctgcgcc cagaggcgtg ccggccagcg gcgggggggcg cagtgcacac gagggggctg   120
gacttcgcct gtgat                                                    135

<210> SEQ ID NO 29
<211> LENGTH: 72
<212> TYPE: DNA
<213> ORGANISM: Artificial sequence
<220> FEATURE:
<223> OTHER INFORMATION: Chemically synthesized

<400> SEQUENCE: 29
atctacatct gggcgccctt ggccgggact tgtggggtcc ttctcctgtc actggttatc     60
accctttact gc                                                         72

<210> SEQ ID NO 30
<211> LENGTH: 336
<212> TYPE: DNA
<213> ORGANISM: Artificial sequence
<220> FEATURE:
<223> OTHER INFORMATION: Chemically synthesized

<400> SEQUENCE: 30
agagtgaagt tcagcaggag cgcagacgcc cccgcgtacc agcagggcca gaaccagctc     60
tataacgagc tcaatctagg acgaagagag gagtacgatg tttttggacaa gagacgtggc   120 cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca ggccctgccc cctcgc                              336

<210> SEQ ID NO 31
<211> LENGTH: 81
<212> TYPE: DNA
```

```
<213> ORGANISM: Artificial sequence
<220> FEATURE:
<223> OTHER INFORMATION: Chemically synthesized

<400> SEQUENCE: 31
ttttgggtgc tggtggtggt tggtggagtc ctggcttgct atagcttgct agtaacagtg    60
gcctttatta ttttctgggt g                                              81

<210> SEQ ID NO 32
<211> LENGTH: 129
<212> TYPE: DNA
<213> ORGANISM: Artificial sequence
<220> FEATURE:
<223> OTHER INFORMATION: Chemically synthesized

<400> SEQUENCE: 32
aggagtaaga ggagcaggct cctgcacagt gactacatga acatgactcc ccgccgcccc    60
gggcccaccc gcaagcatta ccagccctat gccccaccac gcgacttcgc agcctatcgc   120
tccatcgat                                                           129

<210> SEQ ID NO 33
<211> LENGTH: 126
<212> TYPE: DNA
<213> ORGANISM: Artificial sequence
<220> FEATURE:
<223> OTHER INFORMATION: Chemically synthesized

<400> SEQUENCE: 33
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 34
<211> LENGTH: 456
<212> TYPE: DNA
<213> ORGANISM: Artificial sequence
<220> FEATURE:
<223> OTHER INFORMATION: Chemically synthesized

<400> SEQUENCE: 34
atggtgcatg cgaccagccc gctgctgctg ctgctgctgc tgagcctggc gctggtggcg    60
ccgggcctga gcgcgcgcaa atgcagcctg accggcaaat ggaccaacga tctgggcagc   120
aacatgacca ttggcgcggt gaacagccgc ggcgaattta ccggcaccta tattaccgcg   180
gtgaccgcga ccagcaacga aattaaagaa agcccgctgc atggcaccca gaacaccatt   240
aacaaacgca cccagccgac ctttggcttt accgtgaact ggaaatttag cgaaagcacc   300
accgtgttta ccggccagtg cttttattgat cgcaacggca agaagtgct gaaaaccatg   360 tggctgctgc gcagcagcgt gaacgatatt ggcgatgatt ggaaagcgac ccgcgtgggc   420
attaacattt tacccgcct gcgcacccag aaagaa                              456
```

UNIVERSAL IMMUNE RECEPTOR EXPRESSED BY T CELLS FOR THE TARGETING OF DIVERSE AND MULTIPLE ANTIGENS

CROSS-REFERENCE TO RELATED APPLICATION

This application is the U.S. national phase application filed under 35 U.S.C. §371 claiming benefit to International Patent Application No. PCT/US2012/056901, filed on Sep. 24, 2012, which is entitled to priority under 35 U.S.C. §119(e) to U.S. Provisional Application Ser. No. 61/537,933, filed Sept. 22, 2011, each of which is hereby incorporated by reference in its entirety.

BACKGROUND OF THE INVENTION

Adoptive cell transfer (ACT) therapy using bioengineered T cells continues to show significant promise in the treatment of cancer. To this end, investigators at academic and government centers have tested the concept of chimeric antigen receptors (CARs) in advanced cancer. A CAR is a single unit immune receptor of fixed specificity generally comprised of an extracellular antigen-specific antibody fragment coupled to intracellular T cell-signaling domains (Eshhar et al., 1993, Proc. Natl. Acad. Sci. USA 90:720-724). In recent trials, dramatic eradication of refractory chronic lymphocytic leukemia, where all tumor cells express CD19, was achieved by CD19-specific CAR T cell therapy, where all tumor cells express CD19 (Kochenderfer et al., 2010, Blood 116:4099-4120; Porter et al., 2011, N. Engl. J. Med: 365: 725-733). Despite these encouraging results, significant challenges still exist to widespread CAR application. For instance, other tumors are often heterogeneous in antigen expression, differing among individuals, but also in the same patient. Additionally, cancer cells can lose antigen expression by a process of immune-editing, contributing to tumor relapse following initially-effective specific therapy. Targeting a single antigen with CAR therapy may accordingly result in initial tumor regression, but ultimately select for the outgrowth of antigen-loss variants. To facilitate broad clinical application of CARs, scientists have proposed the establishment of a panel of bioengineered T cells with different specificities, custom-made for each individual (Rosenberg et al., 2011, Mol. Ther. 19:1928-1930). Here, each new CAR must be individually created, empirically-tested and produced under clinical-grade conditions; a process that is both technically and economically challenging. The creation of a standardized, distributable immune receptor platform that can be easily tailored for specific antigen-targeting and is amenable to rapid preclinical screening and clinical application would markedly increase accessibility of ACT therapy.

The development of CARs, which bestow T cells with the capacity to recognize cell surface antigens in an MHC unrestricted manner and to receive T cell activation and costimulatory signals, allows for the de novo generation of T cells with potent anti-tumor activity for therapy (Eshhar et al., 1993, Proc. Natl. Acad. Sci. USA 90:720-724). CAR therapy can lead to profound eradication of refractory chronic lymphocytic leukemia and advanced follicular lymphoma, where all tumor cells express, CD19, the target TAA (Kochenderfer et al., 2010, Blood 116:4099-4120; Porter et al., 2011, N. Engl. J. Med: 365:725-733). However, human tumors are often heterogeneous in expression of cell surface antigens, differing markedly not only among individuals but even in the same patient. Further, tumor cells commonly lose cell surface antigen expression during malignant disease progression. Antigen loss is one major factor contributing to tumor relapse following specific therapy that had been initially effective. Alternatively, targeting of TAAs expressed at low levels on normal tissue cells can result in specific toxicity, leading to the retirement of costly vectors. CARs having fixed antigen specificity which are capable of targeting only one TAA may therefore be limited in widespread, continued application as antigen loss variants and toxicity confronted by conventional CAR therapy are not easily addressed by improving binding affinity, cytolytic activity or survival of redirected T cells. Broad application and improved success of CARs in the clinic would necessitate a panel of bioengineered T cells with different specificities, custom-made for each individual. Practically speaking, this approach is technically and economically challenging (Kohn et al., 2011, Mol. Ther. 19:432-438).

Adoptive immunotherapies composed of T cells engineered to express a CAR offer an attractive strategy for treatment of human cancer. However, CARs have a fixed antigen specificity such that only one tumor-associated antigen (TAA) can be targeted, limiting the efficacy that can be achieved due to heterogeneous TAA expression. For this reason, a more generalized and effective application of CAR therapy would benefit from the capability to produce large panels of CARs against many known TAAs.

There is a need in the art for compositions and methods for universal immune receptor (UnivIR) therapies targeting any antigen. The present invention addresses this unmet need in the art.

SUMMARY OF THE INVENTION

The present invention provides an isolated nucleic acid sequence encoding a universal immune receptor (UnivIR), wherein the UnivIR comprises an extracellular label binding domain, a transmembrane domain, a T cell receptor signaling domain. Preferably, the label binding domain binds to a labeled antigen.

In one embodiment, the label binding domain comprises a biotin binding domain and wherein the biotin binding domain binds to a biotinylated antigen.

In one embodiment, the biotin binding domain comprises avidin, or a biotin binding fragment thereof.

In one embodiment, the antigen is selected from the group consisting of a tumor antigen, a self-antigen, a viral antigen, and any combination thereof.

In one embodiment, the UnivIR further comprises an intracellular domain of a costimulatory molecule.

In one embodiment, the intracellular domain of a costimulatory molecule is selected from the group consisting of CD27, CD28, CD2, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof.

In one embodiment, the label binding domain binds to a label selected from the group consisting of myc-tag, FLAG-tag, His-tag, HA-tag, fluorescein isothiocyanate (FITC), dinitrophenol, peridinin chlorophyll protein complex, green fluorescent protein, biotin, phycoerythrin (PE), histidine, streptavidin, avidin, horse radish peroxidase, palmitoylation, nitrosylation, alkalanine phosphatase, glucose oxidase, Glutathione S-transferase (GST), and maltose binding protein.

In one embodiment, the label binding domain binds to a label, wherein the label is selected from the group consisting of a peptide, oligonucleotide, small molecule, and ligand.

The invention also provides an isolated universal immune receptor (UnivIR) comprising an extracellular label binding domain, a transmembrane domain, a T cell receptor signaling domain, wherein the label binding domain binds to a labeled antigen.

The invention also provides a vector comprising a nucleic acid sequence encoding a universal immune receptor (UnivIR), wherein the UnivIR comprises an extracellular label binding domain, a transmembrane domain, a T cell receptor signaling domain, wherein the label binding domain binds to a labeled antigen.

The invention also provides a cell comprising a nucleic acid sequence of sequence encoding a universal immune receptor (UnivIR), wherein the UnivIR comprises an extracellular label binding domain, a transmembrane domain, a T cell receptor signaling domain, wherein the label binding domain binds to a labeled antigen.

In one embodiment, the is selected from the group consisting of a T cell, a Natural Killer (NK) cell, a cytotoxic T lymphocyte (CTL), and a regulatory T cell.

In one embodiment, the cell is activated when the label binding domain binds to its corresponding labeled antigen.

The invention provides a method for stimulating a UnivIR-mediated immune response in a mammal. In one embodiment, the method comprising administering to a mammal an effective amount of a cell genetically modified to express a universal immune receptor (UnivIR), wherein the UnivIR comprises an extracellular label binding domain, a transmembrane domain, a T cell receptor signaling domain, wherein the label binding domain binds to a labeled antigen.

In one embodiment, distinct antigens are targeted sequentially or simultaneously.

In one embodiment, the label binding domain comprises a biotin binding domain and wherein the biotin binding domain binds to a biotinylated antigen.

In one embodiment, the biotin binding domain comprises avidin, or a biotin binding fragment thereof.

In one embodiment, the label binding domain binds to a labeled antigen selected from the group consisting of a tumor antigen, a self-antigen, a viral antigen, and any combination thereof.

In one embodiment, the cell is an autologous cell.

In one embodiment, the method further comprises administering an antigen binding composition to the mammal, wherein the antigen binding composition comprises a label.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A is a schematic representation depicting the avidin-based Immune Receptor gene constructs containing extracellular avidin as a monomer (mcAV) or dimer (dcAv) fused to the human CD3z cytosolic domain alone (BBIR-z) or in combination with the CD28 costimulatory module (BBIR-28z). FIG. 2B is a series of graphs depicting BBIR expression (open histograms) detected via GFP expression for mcAv constructs, or anti-avidin antibody for dcAV constructs. Staining was done 5 days after transduction with lentivirus and compared with untransduced T cells (grey filled histograms). Percent BBIR transduction is indicated. FIG. 2C is a graph depicting how biotin-redirected dcAV but not mcAV.BBIR T cells secrete IFNγ in response to plate-bound biotinylated, but not non-biotinylated, antibody, or scFv (10 ng) in overnight culture. Concentration of IFNγ was expressed as mean±SEM in pg/mL from triplicate wells. FIG. 2D is a graph depicting how dcAv.BBIR-z-and dcAv.BBIR-28z-transduced T cells specifically react against immobilized biotinylated-IgG1. Biotin-redirected dcAv.BBIR-z and dcAv.BBIR-28z T cells secrete IFNγ in response to plate-bound biotinylated antibody in overnight culture at the lowest concentration of 1 ng per well. dcAv.BBIR-z, dcAv.BBIR-28z T cells, or control GFP cells ($10^5$ cells per well) were incubated with plate-immobilized antibody at a concentration range 0 to 100 ng per well. Concentration of IFNγ is expressed in pg/mL (means±SEM; n=3).

FIG. 3, comprising FIG. 3B is a series of graphs depicting biotinylated specific molecules retention on the BBIR T-cell surface as assessed by flow cytometry. BBIR T cells were incubated with 10 ng biotinylated reagents Biotin-APC or P4 Biobody (open histograms) and compared with untransduced control T cells (grey). FIG. 3C is a graph depicting how BBIRs exhibit effector functions in the presence of free biotin at physiologic concentration. BBIR T cells were incubated overnight with Bio-K1 Ab or P4 Biobody painted immobilized mesothelin protein or only with plate-bound biotinylated Abs in the presence of the indicated concentration of biotin. Concentration of IFNγ is expressed as mean±SEM in pg/mL from triplicate wells. FIG. 3D is a series of graphs depicting how BBIR T cells exhibit effector functions against painted cell surface tumor antigens in the presence of antigen-specific biotinylated antibodies. Left, BBIR T cells respond against painted EpCAM on A1847 cancer cell surface. dcAv.BBIR-28z⁺ or control GFP T cells (105) were cultured with an equal number of human A1847 unlabeled or labeled with biotinylated anti-EpCAM Ab (0 up to 1,000 ng). After overnight incubation, cell-free supernatants were analyzed for human IFNγ by ELISA. Results depict the mean±SEM of triplicate wells. Top right, detectable surface EpCAM expression (open histograms) after labeling with different concentrations of biotinylated EpCAM Ab was evaluated by flow cytometry. Bottom right, correlation of detectable Bio-EpCAM MFI on EpCAM⁺ tumors was plotted versus the production of IFNγ by BBIR-28z T cells when cocultured with labeled cancer cells.

FIGS. 4A-4B, depicts how BBIR⁺ T cells exhibit effector functions against various painted cell surface tumor antigens in the presence of antigen-specific biotinylated antibodies. FIG. 4A is a series of graphs depicting how BBIR T cells exhibit effector functions against multiple antigen specificities. BBIR or GFP-transduced T cells were cultured overnight with an equal number of antigen-negative AE17, AE17/mesothelin⁺, AE17/Folate binding protein (FRα)⁺, or A1847 cancer cells. Cell-free supernatant from 3 independent cultures was harvested after overnight incubation and IFNγ levels were measured by ELISA. Mean IFNγ concentration±SEM (pg/mL) is shown. FIG. 4B is a series of graphs depicting how BBIR T cells can be redirected toward different antigens sequentially. BBIR T cells were cultured with GFP-transduced EpCAM⁺ A1847 and AE17/FRα⁺ cell lines at a 1:1:1 ratio. After addition of Bio-EpCAM Ab to cultures for 10 hours, CD3-negative cells were analyzed by FACS to detect for the presence of GFP-transduced EpCAM⁺ A1847 cells. A second Bio-MOV18Ab (anti-FRα) was then added to culture for an additional 10 hours, and FACS was repeated to measure for remaining CD3-negative, GFP-negative AE17/FRα⁺ cells. Left, histograms are shown. Right, results of tumor cell count analysis of pretreated cultures (pre) and after sequential Bio-EpCAM Ab and Bio-MOV18 Ab targeting of A1847 and AE17/FRα⁺ cells, respectively.

FIGS. 5A-5C, depicts the activity of dcAv.BBIR-28z engineered T cells. FIG. A is a series of graphs depicting how dcAv.BBIR-28z⁺ T lymphocytes produce inflammatory cytokines in response to painted A1847 tumor cells with biotinylated antibodies: anti-mesothelin (Bio-K1) and/or anti-EpCAM (Bio-EpCAM). BBIR T cells produced equal levels of (right) IFNγ and (left) Th1 cytokines in response to painted A1847 cells compared with conventional anti-mesothelin P4-28z CAR⁺ T cells. Left, overnight culture supernatants were analyzed for human IFNγ cytokine by ELISA. Concentration of IFNγ is expressed as mean±SEM in pg/mL from triplicate wells. Right, cytokine bead array analysis of cytokine production by dcAv.BBIR-28z⁺ T cells or P4-28z CAR⁺ T cells. Supernatants from 3 independent cultures were pooled and assessed after 16 hours. FIG. 4B is a graph depicting the antigen-specific tumor killing by mesothelin or EpCAM-redirected BBIRs. FIG. 4C is a graph depicting the antigen-specific tumor killing by EpCAM-redirected BBIRs. Primary human T cells transduced to express P4-28z CAR or dcAv.BBIR-28z were cocultured with Cr⁵¹-labeled A1847 cells with painted mesothelin (Bio-K1, FIG. 5A) or EpCAM (Bio-EpCAM, FIG. 5B) for 17 hours at the indicated effector-to-target (E:T) ratio. Percent specific target cell lysis was calculated as (experimental−spontaneous release)−(maximal−spontaneous release)×100. Data represent the means±SD for 3 different experiments. *, P≤0.005 comparing BBIR⁺/Bio-K1 and BBIR⁺/Bio-IgG1T cells. , P≤0.005 comparing BBIR⁺ and P4 CAR⁺ T cells and *, P≤0.005 comparing BBIR⁺/Bio-EpCAM and BBIR⁺/Bio-IgG1 T cells. The difference between the cytotoxic activity was statistically significant at given E:T ratio.

Figure 1:
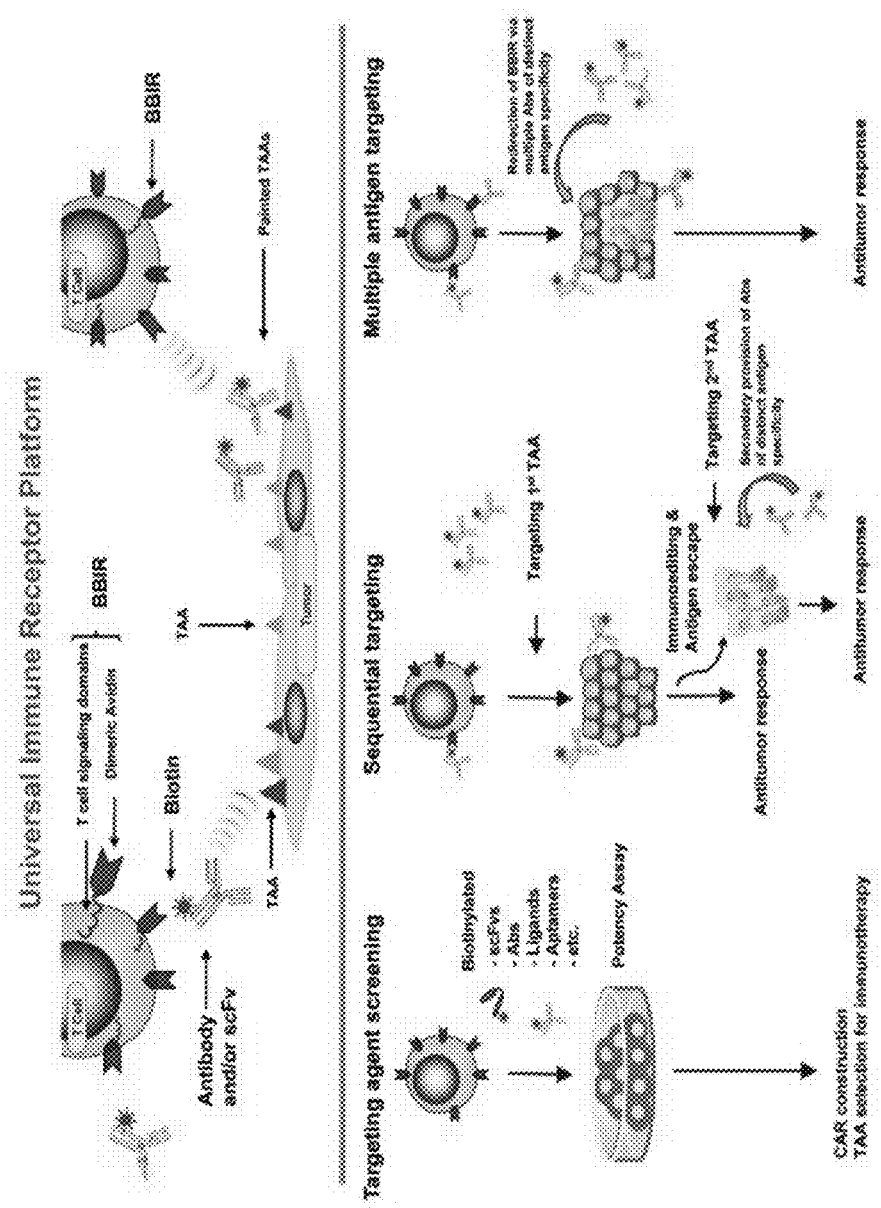
FIG. 1 is a schematic illustration depicting the universal immune receptor platform. (Upper) Schematic of biotin binding immunoreceptor (BBIR) comprised of a dimeric form of chicken avidin protein fused to the T cell signaling domains interacting with a biotinylated tumor associated antigen (TAA) specific molecule. Biotinylated antigen-specific molecules are either pre-targeted to antigen or co-administered with BBIR T cell to enable redirection of BBIRs against a chosen antigen(s). (Lower) A schematic representation of in vitro and in vivo application of BBIR platform. (Left) BBIR platform allows for rapid in vitro screening of candidate targeting agents (scFvs, ligands, aptamers, etc.) for future application, e.g., UnivIR construction. (Middle) The BBIR-engineered T cell strategy for sequentially targeting antigens. If the antigen escapes and tumor recurrence occurs after primary antigen targeting, BBIR T cells can be consecutively redirected against a different TAA by secondary administration of an antibody of distinct specificity. (Right) The BBIR platform allows for simultaneous targeting multiple TAAs to efficiently attack tumors with highly heterogeneous TAA expression FIG. 2, comprising

FIG. 13 is an image demonstrating the reactivity of dcAv BBIR against immobilized antigen mesothelin painted with BioP4 Biobody. Primary human T cells expressing BBIR-z, BBIR-28z and/or BBIR-BBz specifically react against immobilized antigen human mesothelin painted with anti mesothelin biotinylated BioP4 scFv, but not against mesothelin painted with non-biotinylated BioP4scFv. Incorporation of the CD28 or 41BB co-stimulatory modules into BBIR-28z and BBIR-BBz allows transduced T cells to secrete more IFNγ than BBIR-z after specific stimulation.

DETAILED DESCRIPTION

The invention relates to compositions and methods for adoptive T cell therapy in treating a variety of disorders including cancer, infections, and autoimmune disorders. The present invention relates to a strategy of adoptive cell transfer of T cells modified to express a type of immune receptor referred herein as universal immune receptor or UnivIR. One type of UnivIR of the invention is a biotin-binding immune receptor (BBIR). The UnivIR of the invention are molecules that combine specificity for a desired antigen with a T cell receptor-activating intracellular domain to generate a chimeric protein that exhibits a specific immune activity. In one embodiment, the UnivIR of the invention comprises an extracellular label binding domain, a transmembrane domain, and a cytoplasmic domain or otherwise an intracellular domain.

The present invention provides a UnivIR strategy through the incorporation of a label binding domain into the extracellular domain of the UnivIR. The label binding domain targets the UnivIR to any antigen which is labeled with a known label. In one embodiment, the antigen is labeled with biotin, and thus the UnivIR comprises an extracellular domain comprising a biotin binding domain.

In one embodiment, the biotin binding domain comprising UnivIR is referred to as a biotin binding immune receptor (BBIR). The use of UnivIRs (e.g., BBIRs) and so modified T cells provides a flexible system to target any antigen. In one embodiment, the antigen of interest is biotinylated by administration of an antigen binding composition which contains a biotin moiety. For example, in one embodiment, the antigen is biotinylated by the binding of biotin labeled antibody, or fragment thereof, to the antigen. Redirection of BBIR T cells against an antigen is dependent upon intermediate interaction with bound biotinylated antigen-binding molecules. However, the invention is not limited to an antigen that is biotinylated. Rather, the invention encompasses any targeting agent that is biotinylated, including but is not limited to an antibody (e.g., scFv), an oligonucleotide, an aptamer, a receptor, a ligand, and the like.

In one embodiment, the UnivIR platform allows T cells to generate an immune response against a desired antigen either simultaneously or sequentially. The flexibility in antigen-specificity afforded by UnivIR allows for sequential redirection from one antigen to another antigen of distinct specificity. For example, UnivIRs can be redirected from first targeting and eliminating a subset of tumor cells expressing a first antigen to additionally targeting and killing residual tumor cells expressing a second antigen, which had survived the first wave of targeting against the first antigen.

In one embodiment, the invention relates to genetically modified T cells expressing a UnivIR for the treatment of a patient with cancer. The present invention is based upon the finding that the inclusion of the label binding domain within the extracellular domain of a BBIR provides a flexible immunotherapy system that induces antigen specific immune responses. In one embodiment, the UnivIR comprising the label binding domain induces anti-tumor activity. In one embodiment, the UnivIR comprising the label binding domain allows sequential antigen targeting. In one embodiment, UnivIR comprising the label binding domain allows simultaneous antigen targeting of multiple antigens. The UnivIR of the invention provides targeting of any antigen associated with any disease, disorder, or condition. In one embodiment, the antigen is a tumor associated antigen (TAA). In another embodiment, the antigen is a viral antigen. In another embodiment, the antigen is a self-antigen. As such, the present invention includes methods of treating a wide variety of diseases, disorders, and conditions including, but not limited to, cancer, chronic infection, and autoimmune disorders.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Current gene-engineered cellular therapy is restricted in antigen specificity, patient accessibility, and tumor or cell type. The present invention relates to an innovative technological strategy that incorporates TCR and co-stimulatory signals and allows single transfected T-cells to have near infinite antigen specificities. For this purpose, T cells have been equipped with a universal immune receptor redirected against biotinylated antigen-specific molecules (Biotin Binding Immune Receptor; BBIR), including; monoclonal antibodies, scFvs or other tumor specific ligands. This pioneering strategy allows for the first time flexibility in T cell targeted antigen-specificity.

The present invention provides compositions and methods for treating diseases or disorders associated with expression of an antigen, including but is not limited to viral antigens, self-antigens, and the like. In one embodiment, the invention provides compositions and methods for treating cancer, as well as other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., T cell) engineered to express a UnivIR. In one embodiment, the UnivIR of the invention is engineered to comprise an extracellular label binding domain linked to an intracellular T cell signaling domain. Preferably, the UnivIR comprises an extracellular-modified avidin linked to an intracellular T cell signaling domain (referred herein as BBIR; biotin-binding immune receptor). This is because the present invention is based on the discovery that incorporation of a label binding domain provides a flexible and universal strategy for antigen targeting that retains antigen-specific immune responses.

In one embodiment, the label is biotin, and the BBIR comprises a biotin binding domain. In one embodiment, the biotin binding domain comprises avidin. In one embodiment, the BBIR of the invention is targeted to any biotinylated antigen. In one embodiment, antigens are biotinylated by the binding of a biotin-labeled antigen binding composition to the antigen.

However, the present invention is not limited to biotin labels. Rather the invention relates to the use of any known set of binding partners which directs a UnivIR to a labeled antigen. For example, the antigen is labeled with one binding partner, while the UnivIR comprises an extracellular domain comprising the other binding partner. A skilled artisan is aware of such sets of binding partners that could be exploited for use in the present invention. Non-limiting examples of other labels include GST, myc-tag, FLAG-tag, His-tag, and HA-tag. The invention further encompasses the use of known protein-protein interactions, complementary oligonucleotides, and receptor-ligand interactions.

In some embodiments, the present invention is directed to a retroviral or lentiviral vector encoding a UnivIR that is stably integrated into a T cell and stably expressed therein. In other embodiments, the present invention is directed to an RNA encoding UnivIR that is transfected into a T cell and transiently expressed therein. Transient, non-integrating expression of UnivIR in a cell mitigates concerns associated with permanent and integrated expression of UnivIR in a cell.

The UnivIR platform of the invention represents a "universal immune receptor" approach for the targeting of gene-modified T cells to diverse and multiple antigens via interaction with antigen-bound labeled (e.g., biotinylated) molecules, either simultaneously or sequentially. The platform of the invention is applicable with virtually any biotinylated molecule including but not limited to ligands, receptors, oligonucleotides, aptamers, and/or single chain TCRs. The universal immune receptors or UnivIRs of the invention represent a new platform for the rapid screening and generation of redirected T cells with function against virtually any antigen for which a specific targeting agent exists, and thus holds potential for widespread application.

Compositions

The present invention provides a type of UnivIR comprising an extracellular and intracellular domain. The extracellular domain comprises a target-specific binding element otherwise referred to as an extracellular label binding domain. In some embodiments, the extracellular domain also comprises a hinge domain. The intracellular domain or otherwise the cytoplasmic domain comprises, a costimulatory signaling region and a zeta chain portion. The costimulatory signaling region refers to a portion of the UnivIR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the UnivIR, or between the cytoplasmic domain and the transmembrane domain of the UnivIR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a UnivIR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the UnivIR.

Preferably, the UnivIR comprises an extracellular domain, a transmembrane domain and a cytoplasmic domain. The extracellular domain and transmembrane domain can be derived from any desired source of such domains.

Extracellular Label Binding Domain

The extracellular domain of the UnivIR of the present invention comprises a label binding domain. The label binding domain comprises any domain known to bind to a known label. In one embodiment, the label is biotin, and thus the label binding domain comprises a biotin binding domain. In one embodiment, the biotin binding domain comprises an anti-biotin antibody, or fragment thereof. In one embodiment, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

In one embodiment, the biotin binding domain comprises avidin, or a biotin binding fragment thereof. The present invention is based upon a universal strategy of adoptive T cell therapy using biotin-directed UnivIRs targeted to a biotinylated antigen. In one embodiment, the biotin binding domain comprises streptavidin, or biotin binding fragment thereof. Avidin and streptavidin are proteins known to have a high affinity for biotin. In one embodiment, the binding domain comprises a dimerized avidin domain, as it is shown herein that a UnivIR comprising a dimerized avidin domain efficiently recognized biotinylated antigens. In another embodiment, the biotin binding domain comprises a monomeric avidin domain. However, the present invention is not limited to biotin binding domains comprising avidin, streptavidin, or fragments thereof. Rather, any domain known to bind biotin is encompassed in the present invention. Further, any domain found in the future to bind to biotin is also encompassed in the present invention.

Further, the present invention relates to a UnivIR strategy wherein the UnivIR comprises an extracellular domain that is targeted to any labeled antigen. Therefore, the present invention is not limited to a biotin binding domain comprising UnivIR directed to a biotin labeled antigen. Rather, any system of labeled antigen targeted by a label-binding domain comprising UnivIR is encompassed herein. [[For example, the present invention encompasses the use of protein-protein interactions, receptor-ligand interactions, complementary oligonucleotides, and the like, to direct the UnivIR to the target antigen. Examples of other types of labels useful in the present invention include myc-tag, FLAG-tag, His-tag, HA-tag, fluorescein isothiocyanate (FITC), dinitrophenol, peridinin chlorophyll protein complex, green fluorescent protein, biotin, phycoerythrin (PE), histidine, streptavidin, avidin, horse radish peroxidase, palmitoylation, nitrosylation, alkalanine phosphatase, glucose oxidase, Glutathione S-transferase (GST), maltose binding protein, and any types of fluorescent materials including quantum dot nanocrystals.

In one embodiment, the antigen of interested is labeled, for example, by the administration of an antigen binding composition which comprises the label. In one embodiment, the label-directed UnivIR comprises an extracellular domain comprising a label-binding domain. Non-limiting examples of label binding domains include peptides, antibodies, nucleotides, small molecules, and fragments thereof, known to bind to the label. In one embodiment, the label binding domain of the UnivIR is translated along with the intracellular and transmembrane domains of the UnivIR. In another embodiment, the label binding domain is applied to the UnivIR following translation. For example, in one embodiment, the label binding domain is a distinct composition, separate from the intracellular and transmembrane domains of the UnivIR, which then binds to the UnivIR, thereby forming a complex.

As discussed elsewhere herein, incorporation of a biotin binding domain into the UnivIR allows for a universal design that can be targeted to any desired antigen. For example, when an antitumor UnivIR is desired, an antigen that is associated with a tumor is labeled with biotin, and the biotin binding domain of the UnivIR therefore directs the UnivIR to the biotin labeled tumor antigen. The tumor may be any type of tumor as long as it has a cell surface antigen which may be labeled and thus is recognized by the UnivIR.

In one embodiment, the UnivIR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the UnivIR of the invention include those associated with viral, bacterial and parasitic infections, autoimmune disease and cancer cells.

In one embodiment, the retroviral or lentiviral vector comprising comprises a UnivIR designed to be directed to an antigen of interest by way of engineering a label binding domain (e.g., biotin binding domain) into the UnivIR. In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The present invention is not limited to UnivIRs directed to tumor antigens. Rather any antigen associated with a disease or disorder may be targeted by the UnivIR of the invention. For example, in one embodiment, the UnivIR of the invention is targeted to a viral antigen. In another embodiment, the UnivIR of the invention is targeted to a self antigen. Self antigens are antigens normally tolerated by a healthy subject, but induce an adaptive immune response in autoimmune disorders. For example, epidermal cadherin is a self antigen which induces an autoimmune response in pemphigus vulgaris. Other non-limiting self antigens (listed with their associated autoimmune disorder) which are useful to be targeted by the composition of the invention, include pancreatic β-cell antigen (insulin-dependent diabetes mellitus), acetylcholine receptor (*Myasthenia gravis*), thyroid-stimulating hormone receptor (Graves' disease), insulin receptor (hypoglycemia), glycoprotein IIb/IIIa (immune thrombocytopenic purpura), Rh blood group antigens (autoimmune hemolytic anemia), rheumatoid factor IgG complexes (rheumatoid arthritis), and myelin basic protein (experimental autoimmune encephalomyelitis, multiple sclerosis). In one embodiment, an immunosuppressive T regulatory cell modified to express a UnivIR targeted via a biotin binding domain to a self-antigen reduces the autoimmune response directed to the self antigen.

Transmembrane Domain

With respect to the transmembrane domain, the UnivIR can be designed to comprise a transmembrane domain that is fused to the extracellular domain of the UnivIR. In one embodiment, the transmembrane domain that naturally is associated with one of the domains in the UnivIR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the UnivIR. A glycine-serine doublet provides a particularly suitable linker.

Cytoplasmic Domain

The cytoplasmic domain or otherwise the intracellular signaling domain of the UnivIR of the invention is responsible for activation of at least one of the normal effector functions of the immune cell in which the UnivIR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the UnivIR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the UnivIR of the invention comprises a cytoplasmic signaling sequence derived from CD3 zeta.

In a preferred embodiment, the cytoplasmic domain of the UnivIR can be designed to comprise the CD3-zeta signaling domain by itself or combined with any other desired cytoplasmic domain(s) useful in the context of the UnivIR of the invention. For example, the cytoplasmic domain of the UnivIR can comprise a CD3 zeta chain portion and a costimulatory signaling region. The costimulatory signaling region refers to a portion of the UnivIR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the UnivIR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta. In another embodiment, the cytoplasmic domain is designed to comprise any combination of CD3-zeta, CD28, 4-1BB, and the like.

Labeling of Antigens

The present invention encompasses a UnivIR directed to a labeled antigen. In one embodiment, the antigen is labeled with biotin, and the UnivIR comprises a biotin binding domain. The antigen of interest is labeled by any method known in the art. For example, in one embodiment, an antigen binding composition, comprising a label (e.g. biotin), is applied to the antigen. The composition may be, for example, an antibody, an antibody fragment, a peptide, a nucleic acid, aptamer, ribozyme, small molecule, and the like. In some aspects, an antigen binding composition lacking a label may be used as the antigen binding composition. For example, in one embodiment, the antigen binding composition lacks a label while a second composition, which binds the antigen binding composition, contains the label.

As discussed elsewhere herein, the present invention is not limited to the label being biotin. Rather any known set of binding partners may be used to target the UnivIR to an antigen of interest. Non-limiting examples of labels include a peptide, an oligonucleotide, a small molecule, and a ligand. Well-known examples of labels include myc-tag, FLAG-tag, His-tag, HA-tag, fluorescein isothiocyanate (FITC), dinitrophenol, peridinin chlorophyll protein complex, green fluorescent protein, biotin, phycoerythrin (PE), histidine, streptavidin, avidin, horse radish peroxidase, palmitoylation, nitrosylation, alkalanine phosphatase, glucose oxidase, Glutathione S-transferase (GST), maltose binding protein, and any types of fluorescent materials including quantum dot nanocrystals.

In some embodiments, the antigen is labeled by way of the addition of a peptide domain, wherein the UnivIR comprises an extracellular domain which selectively binds to the peptide domain. In another embodiment, the antigen is labeled by way of the addition of a ligand, wherein the UnivIR comprises an extracellular domain comprising a receptor, or portion thereof, which selectively binds to the ligand. In yet another embodiment, the antigen is labeled by way of an oligonucleotide, wherein the UnivIR comprises an extracellular domain comprising a complementary oligonucleotide.

Labeling of the antigen with any of such labels may be performed directly or indirectly by way of a labeled antigen binding composition. The label may be conjugated to the antigen binding composition using techniques such as chemical coupling and chemical cross-linkers. Alternatively, polynucleotide vectors can be prepared that encode the labeled antigen binding compositions as fusion proteins. Cell lines can then be engineered to express the labeled antigen binding compositions, and the labeled antigen binding compositions can be isolated from culture media, purified and used in the methods disclosed herein. Biotinylation of antigen binding compositions can be prepared from biotin-NHS (N-hydroxy-succinimide) using techniques well-known within the art (e.g., biotinylation kit, Pierce Chemicals, Rockford).

The labeled antigen binding compositions may be formulated for administered to a subject using techniques known to the skilled artisan. Formulations of the labeled antigen binding compositions may include pharmaceutically acceptable excipient(s). Excipients included in the formulations will have different purposes depending, for example, on the nature of the label, the antigen binding composition, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

In another embodiment, the universal immune receptor comprises an extracellular domain that binds to an unlabeled intermediate, which in turn binds the agent or antigen.

Vectors

The present invention encompasses a DNA construct comprising the sequence of a UnivIR, wherein the sequence comprises the nucleic acid sequence of an extracellular domain operably linked to the nucleic acid sequence of an intracellular domain. In one embodiment, the extracellular domain comprises a label binding domain. An exemplary extracellular domain comprises a biotin binding domain, for example a dimerized avidin domain. An exemplary intracellular domain that can be used in the UnivIR of the invention includes but is not limited to the intracellular domain of CD3-zeta, CD28, 4-1BB, and the like. In some instances, the UnivIR can comprise any combination of CD3-zeta, CD28, 4-1BB, and the like.

In one embodiment, the UnivIR of the invention comprises a dimerized avidin domain, human CD8 hinge and transmembrane domain, and a CD3-zeta signaling domains.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding UnivIRs is typically achieved by operably linking a nucleic acid encoding the UnivIR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a UnivIR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000

FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA UnivIR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the UnivIR of the present invention. For example, the template for the RNA UnivIR comprises an extracellular domain comprising a label binding domain; a transmembrane domain comprising the hinge and transmembrane domain of CD8a; and a cytoplasmic domain comprises the signaling domain of CD3-zeta.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the UnivIR sequences are delivered into cells using a retroviral or lentiviral vector. UnivIR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the UnivIR sequences are delivered into cells using in vitro transcribed mRNA. In vitro transcribed mRNA UnivIR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some WT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the Med-Pulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable UnivIR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a UnivIR that combines a label binding domain with an intracellular domain of a T cell receptor. In some instances, the UnivIR further comprises an intracellular domain of one or more co-stimulatory molecule. Therefore, in some instances, the modified T cell can elicit a UnivIR-mediated T-cell response.

The invention provides the use of a UnivIR to redirect the specificity of a primary T cell to a labeled antigen. Thus, the present invention also provides a method for stimulating a T cell-mediated immune response to a target cell population or tissue in a mammal comprising the steps of labeling the target antigen and administering to the mammal a T cell that expresses a UnivIR, wherein the UnivIR comprises a binding moiety that specifically interacts with the labeled target, an intracellular domain of a TCR (e.g., intracellular domain of human CD3zeta), and a costimulatory signaling region.

[[In one embodiment, labeling of the target antigen comprises administering to the mammal an antigen binding composition which comprises a label. Administration of the T cell and the labeling of the antigen may occur in any order. For example, in one embodiment, the labeled antigen binding composition is administered to the mammal prior to administration of the T cell. In another embodiment, the T cell is administered to the mammal prior to administration of the labeled antigen binding composition.

The labeled antigen binding compositions may be administered to a subject using modes and techniques known to the skilled artisan. Exemplary modes include, but are not limited to subcutaneously, intradermally, intratumorally, intranodally, intramedullary, intramuscularly, by intravenous (i.v.) injection, intra-arterial, intracardiac, intra-articular, intra-synovial, intracranial, intraspinal, intrathecal or intraperitoneally. In one embodiment, the labeled compositions are administered to a patient by intradermal or subcutaneous injection. In another embodiment, the labeled compositions of the present invention are preferably administered by i.v. injection. The labeled compositions may be injected directly into a tumor, lymph node, or site of infection. The labeled compositions are administered in an amount which is effective for labeling the target antigen and is effective for treating the patient. The particular amount administered to the subject will vary between wide limits, depending upon the location, source, identity, extent and severity of the disorder, the age and condition of the individual to be treated, etc.]]

In one embodiment, the present invention includes a type of cellular therapy where T cells are genetically modified to express a UnivIR and the UnivIR T cell is infused to a recipient in need thereof. The infused cell is able to kill tumor cells in the recipient Unlike antibody therapies, UnivIR T cells are able to replicate in vivo resulting in long-term persistence that can lead to sustained tumor control.

While the data disclosed herein specifically disclose lentiviral vectors encoding a dimerized avidin domain, along with human CD8a hinge and transmembrane domain, and human CD28 and CD3zeta signaling domains, the invention should be construed to include any number of variations for each of the components of the construct as described elsewhere herein. That is, the invention includes the use of any label binding domain in the UnivIR to generate a UnivIR-mediated T-cell response specific to a target antigen.

The present invention also provides a method of simultaneously targeting a plurality of targets. For example, in one embodiment, a plurality of antigens are labeled, either directly or indirectly. For example, in one embodiment, a plurality of labeled antigen binding compositions, specific for each of the plurality of antigens, is administered to the mammal Administration of a genetically modified T cell expressing a UnivIR comprising a label binding domain allows for the targeting of the modified T cells to each of the plurality of labeled antigens.

The present invention also provides a method of sequential targeting of a plurality of targets. For example, in one embodiment, a first antigen is labeled, either directly or indirectly. For example, in one embodiment, a first labeled antigen binding composition, specific for the first antigen, is administered to the mammal. In one embodiment, the method comprises administering of a genetically modified T cell expressing a UnivIR comprising a label binding domain, thereby targeting the T cell to the first labeled antigen. In one embodiment, the method comprises labeling a second antigen, either directly or indirectly. For example, in one embodiment, a second labeled antigen binding composition, specific for the second antigen, is administered to the mammal. Genetically modified T cells expressing the UnivIR comprising a label binding domain is thus also directed to the second labeled antigen. In one embodiment, the method comprises allowing sufficient time to elapse between administration of the first and second labeled antigen binding composition, to allow for clearance of cells expressing the first antigen prior to directing the T cell to the second antigen. As would be understood by those skilled in the art, the method of the invention encompasses further iterations for the targeting of additional target antigens.

In one embodiment, the present invention provides a method of using a UnivIR to target a labeled antigen for treating cancer. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the UnivIRs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases). In one embodiment, the present invention provides a method of using the UnivIR to target an antigen associated with a virus, bacteria, parasite, or other infection in order to treat the infection.

In one embodiment, the present invention provides a method of using the UnivIR to target a self antigen to treat an autoimmune disorder. In one embodiment, the method comprises genetically modifying an immunosuppressive T regulatory cell to express a UnivIR comprising a label binding domain. In one embodiment comprises labeling a self antigen with a label and administering a T regulatory cell modified to express a UnivIR comprising a label binding domain. In one embodiment, targeting of the T regulatory cell to the self antigen reduces the autoimmune response directed to the self antigen. For example, in one embodiment, activation of the genetically modified T regulatory cell via binding to the targeted self antigen reduces cytolytic T cell proliferation. Non-limiting examples of autoimmune disorders treatable by way of the present invention includes multiple sclerosis, inflammatory bowel disease, Crohn's disease, ulcerative colitis, graft-versus-host disease, rheumatoid arthritis, psoriasis, dermatitis, autoimmune type I diabetes, systemic lupus erythematosus, Hashimoto's thyroiditis, myasthenia gravis, and the like. A would be understood by the skilled artisan, the present invention is useful for treating any autoimmune disorder characterized by an autoimmune response against a self antigen. The present invention encompasses treatment of autoimmune disorders where the self antigen is currently known, and where the self antigen is elucidated in the future.

However, the invention should not be construed to be limited to solely to the antigen targets and diseases disclosed herein. Rather, the invention should be construed to include any antigenic target that is associated with a disease where a UnivIR can be used to treat the disease.

The UnivIR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a UnivIR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a UnivIR disclosed herein. The UnivIR-modified cell can be administered to a mammalian recipient to provide a therapeutic benefit. The mammalian recipient may be a human and the UnivIR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the UnivIR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the UnivIR-modified T cells of the invention.

The UnivIR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. Strategies for T cell dosing and scheduling have been discussed (Ertl et al, 2011, Cancer Res, 71:3175-81; Junghans, 2010, Journal of Translational Medicine, 8:55).

Screening

In one embodiment, the present invention provides a method for screening potential antigen binding compositions, including for example, antibodies, peptides, oligonucleotides, ribozymes, aptamers, and the like. According to one embodiment of the present invention, a T cell modified to express a UnivIR comprising a label binding domain is used screen labeled compositions for the ability of the composition to bind to the target antigen. In one embodiment, a cell based assay comprising the UnivIR-expressing modified T cell is used to screen compositions. In one embodiment, the assay comprises administering a labeled composition to the assay and detecting a detectable response induced by the T cell. For example, in one embodiment, the assay comprises detecting the activation of the T cell. In another embodiment, the assay comprises detecting the level of secreted cytokines. In one embodiment, the target antigen, for which an antigen binding composition is sought, is immobilized on a surface, for example a cell culture plate or a bead. In another embodiment, the assay comprises a cell expressing the target antigen.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

A Universal Strategy for Adoptive Immunotherapy of Cancer Through Use of a Novel T-Cell Antigen Receptor As described herein, a novel strategy to extend the recognition specificity potential of a bioengineered lymphocyte population has been demonstrated, which allows for flexible approaches to redirect T cells against various tumor associated antigens (TAAs). This strategy employed a biotin-binding immune receptor (BBIR) composed of an extracellular-modified avidin linked to an intracellular T cell signaling domain BBIR T cells recognized and bound exclusively to cancer cells pre-targeted with specific biotinylated molecules. The versatility afforded by BBIRs permitted sequential or simultaneous targeting of a combination of distinct antigens. Together, these findings demonstrate that a platform of universal T cell specificity can significantly extend beyond conventional CAR approaches, permitting the tailored generation of T cells of unlimited antigen specificity for improving the effectiveness of adoptive T cell immunotherapies for cancer.

Briefly, experiments were designed to overcome restrictions of current gene-engineered cellular therapy which is restricted in antigen specificity, patient accessibility, and tumor type. Primary human T cells were outfitted with a universal immune receptor redirected against biotinylated antigen-specific molecules (biotin binding immune receptor; BBIR). BBIR T cells specifically recognized and were activated by various biotinylated molecules, including scFvs and antibodies, that were either immobilized on a plate, specifically bound to immobilized antigen or bound to antigen-expressing tumor cells (FIG. 1, upper panel). Redirection of BBIR T cells against protein antigens was dependent upon intermediate interaction with bound biotinylated antigen-binding molecules; non-binding biotinylated molecules had no effect. Importantly, addition of soluble biotin to cultures at physiological levels found in human serum had no inhibitory effect on the specific immunoactivation of BBIR T cells. Furthermore, soluble biotin alone did not cause antigen-independent activation of BBIRs, indicating the need for immobilization and BBIR cross-linking.

BBIR T cells were immunoreactive against tumor-associated antigens (TAAs) expressed on the cell surface, as demonstrated by their production of Th1 cytokines and cytolytic activity when stimulated with ovarian cancer cells painted with a biotinylated anti-EpCAM antibody. A notable secondary benefit to the BBIR platform was its applicability for rapid screening of scFvs to be used in UnivIR construction (FIG. 1, lower). Here, a biotinylated anti-mesothelin scFv permitted BBIR T cell redirection to mesothelin-expressing cancer cells and predicted its utility in a UnivIR construct (Bergan et al., 2007, Cancer Lett. 255:263-274; Lanitis et al., 2012, Mol. Ther. 20:633-643).

The materials and methods employed in these experiments are now described.

Materials and Methods

Biotin-Binding Immune Receptor Construction

Monomeric avidin, DNA sequence was amplified from cDNA obtained from chicken oviduct using primers: 5'-AAAAGCCTAGGATCC-3'(SEQ ID NO: 1) and 5'-AAC-CGCGCTAGCAAA-3' (SEQ ID NO: 2). The nucleotide sequence for the dimeric form of chicken avidin (dcAv) was selected from DDBJ/GenBank™/EBI Data Bank (accessing number AJ616762). After codon optimization for humans and the insertion of 3'-Bam-H1 and 5'-Nhe-1 restriction, the construct was purchased from GeneArt and amplified using primers: 5'-AAAGGATCCGCTAGAAAGAGAAC-3' (SEQ ID NO: 3) and 5'-AAAGCTAGCCTCGGAGAACTTCC-3' (SEQ ID NO: 4). PCR products were digested with Bam-HI and NheI enzymes and ligated into pELNS, a third generation self-inactivating lentiviral expression vector, containing human CD3z or CD28-CD3z signaling endodomains, under an EF-1a promoter. The resulting constructs were designated pELNS GFP 2A mcAv. BBIR-z/CD28z and pELNS dcAv.B-BIR-z/CD28z, respectively.

TABLE 1

Sequence identifiers for BBIR constructs

| SEQ ID NO: # | IDENTITY |
|---|---|
| SEQ ID NO: 5 | dcAV BBIR-Zeta (amino acid sequence) |
| SEQ ID NO: 6 | dcAV BBIR-28zeta (amino acid sequence) |
| SEQ ID NO: 7 | dcAV BBIR-4-1BB (amino acid sequence) |
| SEQ ID NO: 8 | mcAv BBIR-28z (amino acid sequence) |
| SEQ ID NO: 9 | mcAV BBIR-Zeta (amino acid sequence) |
| SEQ ID NO: 10 | mcAv BBIR-4-1BB (amimo acid sequence)t |
| SEQ ID NO: 11 | dcAV BBIR-Zeta (nucleic acid sequence) |
| SEQ ID NO: 12 | dcAV BBIR-28zeta (nucleic acid sequence) |
| SEQ ID NO: 13 | dcAV BBIR-4-1BB (nucleic acid sequence) |
| SEQ ID NO: 14 | mcAv BBIR-28z (nucleic acid sequence) |
| SEQ ID NO: 15 | mcAV BBIR-Zeta (nucleic acid sequence) |
| SEQ ID NO: 16 | mcAv BBIR-4-1BB (nucleic acid sequence) |
| SEQ ID NO: 17 | CD8 leader (amino acid sequence) |
| SEQ ID NO: 18 | Dual Chain Avidin (amino acid sequence) |
| SEQ ID NO: 19 | CD8a Hinge (amino acid sequence) |
| SEQ ID NO: 20 | CD8 TM (amino acid sequence) |
| SEQ ID NO: 21 | CD3z ICD (amino acid sequence) |
| SEQ ID NO: 22 | CD28 TM (amimo acid sequence)t |
| SEQ ID NO: 23 | CD28 ICD (amino acid sequence) |
| SEQ ID NO: 24 | 4-1BB ICD (amino acid sequence) |
| SEQ ID NO: 25 | Monomer chicken Avidin (amino acid sequence) |
| SEQ ID NO: 26 | CD8 leader (nucleic acid sequence) |
| SEQ ID NO: 27 | Dual Chain Avidin (nucleic acid sequence) |
| SEQ ID NO: 28 | CD8a hinge (nucleic acid sequence) |
| SEQ ID NO: 29 | CD8 TM (nucleic acid sequence) |
| SEQ ID NO: 30 | CD3z ICD (nucleic acid sequence) |
| SEQ ID NO: 31 | CD28 TM (nucleic acid sequence) |
| SEQ ID NO: 32 | CD28 ICD (nucleic acid sequence) |
| SEQ ID NO: 33 | 4-1BB ICD (nucleic acid sequence) |
| SEQ ID NO: 34 | Monomer chicken Avidin (nucleic acid sequence) |

Recombinant Lentivirus Production

High-titer replication-defective lentiviral vectors were produced and concentrated as previously described (Song et al., 2011, Cancer Res. 71:4617-1627; Perez et al., 2005, Clin. Immunol. 115:26-32). Briefly, 293T human embryonic kidney cells were transfected with pVSV-G (VSV glycoprotein expression plasmid), pRSV.REV (Rev expression plasmid), pMDLg/p.RRE (Gag/Pol expression plasmid), and pELNS transfer plasmid using Express Inn (Open Biosystems). The viral supernatant was harvested at 24 and 48 h post-transfection. Viral particles were concentrated and resuspended in 0.5 ml by ultracentrifugation for 2.5 h at 25,000 rpm with a Beckman SW28 rotor (Beckman Coulter, Fullerton, Calif.).

T Cells

Primary human CD4+ and CD8+ T cells were isolated from healthy volunteer donors following leukapheresis by negative selection, and purchased from the Human Immunology Core at University of Pennsylvania. All specimens were collected under a University Institutional Review Board-approved protocol, and written informed consent was obtained from each donor. T cells were cultured in complete media (RPMI 1640 supplemented with 10% heat inactivated fetal bovine serum (FBS), 100 U/ml penicillin, 100 ug/ml streptomycin sulfate, 10-mM HEPES), and stimulated with anti-CD3 and anti-CD28 mAbs coated beads (Invitrogen) as described. 24 hr after activation, T cells were transduced with lentiviral vectors at MOI of ~5-10. CD4+ and CD8+ T cells used for in vivo experiments were mixed at a 1:1 ratio, activated, and transduced. Human recombinant interleukin-2 (IL-2; Novartis) was added every other day to 50 IU/ml final concentration and a $0.5-1 \times 10^6$ cells/ml cell density was maintained. Rested engineered T cells were adjusted for identical transgene expression prior to functional assays.

Cell Lines

Lentivirus packaging was performed in the immortalized normal fetal renal 293T cell line purchased from ATCC. Human cell lines used in immune based assays include the established human ovarian cancer cell lines A1847, and mouse malignant mesothelioma cell line, AE17, was transduced with lentivirus to express human mesothelin (AE17-M) or FRα (AE17-FRα). 293T cells and tumor cell lines were maintained in RPMI-1640 (Invitrogen) supplemented with 10% (v/v) heat-inactivated FBS, 2 mM L-glutamine, and 100µg/mL penicillin and 100 U/mL streptomycin. Functional assays were performed in biotin free DMEM medium (Invitorgen) supplemented as described above. All cell lines were purchased from ATCC.

Biotin Binding Analysis

Flow cytometry was performed as described elsewhere herein. In brief, $1 \times 10^6$ mcAV.BBIR-z, dcAv.BBIR-z or mock-transfected T cells were incubated (30 min, 37° C.) with biotin-APC (100 ng/ml) or P4 Biobody (100 ng/ml) in PBS. Cells were washed twice with PBS, and analyzed by FACS. For each sample 10000 cells were counted and analyzed. Binding of biotinylated antibodies to biotin binding immune receptor was also assessed by ELISA. 96-well flat-bottomed microtiter plates (MaxiSorp Immuno microwell plates, Nunc, Roskilde, Denmark) were coated (overnight, 4° C.) with recombinant human mesothelin (1 µg/ml) in 50 µl coating buffer per well. Plates were washed twice in PBS and $1 \times 10^5$ BBIR+ or control T cells were administered per well, previously labeled with animesothelin biotinylated antibodies (as described elsewhere herein for binding assay). After 16 hours, co-culture supernatants were assayed for presence of IFNγ using an ELISA Kit, according to manufacturer's instructions (Biolegend). Values represent the mean of triplicate wells.

Sequential Targeting Assay

To demonstrate sequential killing of target cells by BBIRs (dcAvBBIR-28z), ovarian cancer cell line expressing EpCAM and FRα, A1847 was transduced with lentiviral vector encoding for GFP. Target tumor cell lines A1847/GFP/EpCAM+/FRα+ and AE17/FRα+ were mixed at a 1:1 ratio. For EpCAM redirected killing (first target), tumor cells were incubated with anti-EpCAM biotinylated antibody ($100 \text{ ng}/1 \times 10^6$ cells) for 30 minutes at 37° C., washed and resuspended at $10 \times 10^6$ cells/ml in DMEM medium (Gibco/Invitrogen, Carlsbad, Calif.). Following 10 hour effector:target (5:1) incubation at 37° C. cells were used for FACS analysis. For sequential redirecting against second target FRα expressing tumor cells, remaining tumor cells were harvested, washed and anti-FRα biotinylated antibody was added into the culture (10 ng/ml). Following 10 hour remaining cells were harvested and FACS analysis on CD3 negative population was performed.

Cytokine Release Assays

Cytokine release assays were performed by co-culture of 1×10$^5$ BBIR+ T cells with immobilized Bio-IgG1 or IgG1 as well with Bio-K1, P4 Biobody (100 ng/ml) labeled immobilized recombinant human mesothelin (10 ng/well) or 1×10$^5$ target cells labeled with antigen specific antibodies at 100 ng/10$^6$ cells for 30 min at 4° C., per well in triplicate in 96-well round bottom plates, in a final volume of 200 µl of T cell media. After 16 hours, co-culture supernatants were assayed for presence of IFNγ using an ELISA Kit, according to manufacturer's instructions (Biolegend). Values represent the mean of triplicate wells. IL-2, IL-4, IL-10, TNF-α and MIP-1a cytokines were measured by flow cytometry using Cytokine Bead Array, according to manufacturer's instructions (BD Biosciences).

Cytotoxic Assays $^{51}$Cr release assays were performed as described. Target cells were labeled with the following antibodies; biotinylated-EpCAM and EpCAM (BioLegends) or biotinylated-K1 and K1 (Bio-Legends) at 100 ng per 10$^6$ cells for 30 minutes at 37° C. in PBS/2% FBS. Next, antibody-labeled cells were labeled with 100uCi 100mCi $^{51}$Cr at 37° C. for 1.5 hours. Target cells were washed three times in PBS, resuspended in CM at 10$^5$ viable cells/mL and 100 uL added per well of a 96-well V-bottom plate. Effector cells were washed twice in CM and added to wells at the given ratios. Plates were quickly centrifuged to settle cells, and incubated at 37° C. in a 5% $CO_2$ incubator for 4 or 18 hours after which time the supernatants were harvested, transferred to a lumarplate (Packard) and counted using a 1450 Microbeta Liquid Scintillation Counter (Perkin-Elmer). Spontaneous $^{51}$Cr release was evaluated in target cells incubated with medium alone. Maximal $^{51}$Cr release was measured in target cells incubated with SDS at a final concentration of 2% (v/v). Percent specific lysis was calculated as (experimental–spontaneous lysis/maximal–spontaneous lysis) times 100.

Xenograft Model of Ovarian Cancer

All animals were obtained from the Stem Cell and Xenograft Core of the Abramson Cancer Center, University of Pennsylvania. Six to 12-week-old NOD/SCID/γ-chain−/− (NSG) mice were bred, treated and maintained under pathogen-free conditions in-house under University of Pennsylvania IACUC approved protocols. For an established ovarian cancer model, 6 to 12-week-old female NSG mice were inoculated s.c. with 5×10$^6$ A1847 fLuc+ cells on the flank on day 0. After tumors become palpable at about 1 month, human primary T cell (CD4+ and CD8+ T cells used were mixed at a 1:1 ratio) were activated, and transduced as described above. After 2 weeks of T cell expansion, when the tumor burden was ~150-200 mm$^3$, mice were treated IT with T cells and antibodies (days 45, 48 and 51), or antibodies only (100 ng/day on days 56 and 60). Tumor dimensions were measured with calipers, and tumor volumes calculated using the formula V=½(length×width$^2$), where length is the greatest longitudinal diameter and width is the greatest transverse diameter. In all models, 4 mice were randomized per group prior to treatment.

Flow Cytometric Analysis

The following mAbs were used for phenotypic analysis: APC-Cy7 Mouse Anti-Human CD3; FITC-anti-human CD4; APC-anti-human CD8; (BD Biosciences). Tumor cell surface expression of FR was detected by Mov18/ZEL antibody (Enzo Life Sciences), mesothelin by biotinylated P4 Biobody followed by incubation with Strepavidin-APC and/or biotinylated anti-mesothelin K1 antibody (BioLegend), EpCAM by biotinylated ani-EpCAM. UnivIR expression was detected by FITC-anti-Avidin antibody (LifeBioscience) at 10 ng per 10$^6$ cells. PE-conjugated anti-Bcl-X$_L$ antibody was purchased from Southern Biotech. Isotype matched control Abs were used in all analyses. Flow cytometric data were analyzed by FlowJo software.

Statistical Analysis

Data are expressed as mean±SEM of n experiments. Statistical evaluation was performed by using 2-tailed Student's t test. P values less than 0.05 were considered significant.

The results of the experiments are now described.

Development of a Novel Universal Immune Receptor for Antigen Targeting

Figure 2:
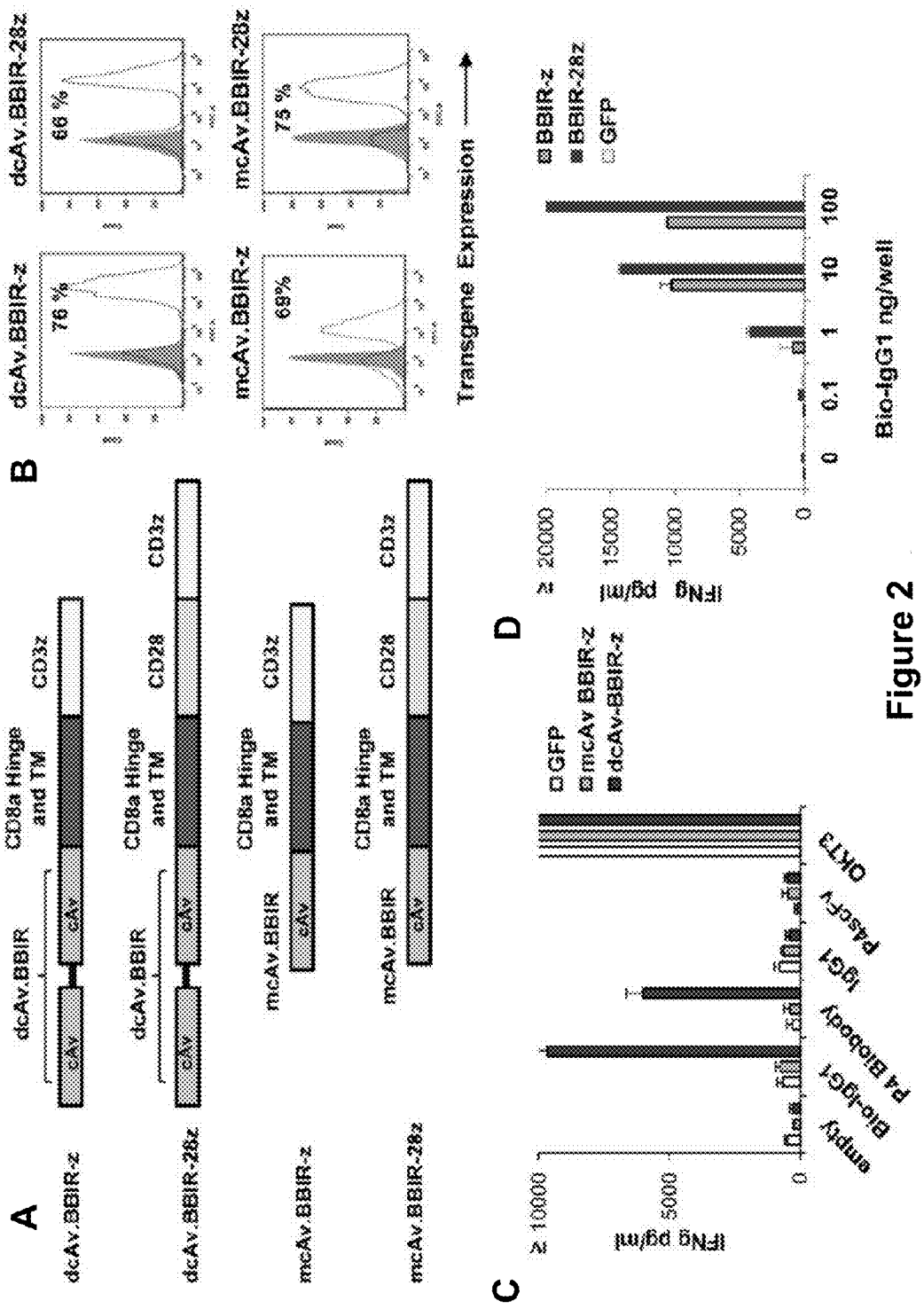
FIGS. 2A-2D, depicts the generation and specific immune recognition by BBIR-transduced human T cells in vitro.

To extend specificity of bioengineered T cells, a universal immune-receptor was developed for flexibility in targeting multiple and diverse antigens of virtually any specificity. A series of pELNS-based recombinant lentiviral vectors were generated encoding a biotin binding immune-receptor (BBIR) comprising extracellular avidin in monomeric (mcAv) or dimeric (dcAv) form, linked to the intracellular human CD3-z chain signaling domain alone or in tandem with CD28, via a CD8α hinge and transmembrane region (FIG. 2A). Lentiviral vectors encoding an anti-mesothelin CAR containing CD28/CD3z endodomains (P4-28Z), or GFP were used as antigen specificity controls (Lanitis et al., 2012, Mol. Ther. 20:633-643). Surface expression of the lentivirus encoded vectors in transduced primary human T cells was determined by flow cytometry. After transduction, BBIR-expressing vectors render efficient transgene expression by CD3/CD28-activated T cells at a range of 60%-80% (FIG. 2B).

To be relevant for tumor therapy, an immune-receptor must be able to redirect the specificity of primary T cells against antigen. First, the ability of BBIR T cells to bind to various biotinylated antigen-specific molecules, including full length antibodies (Ab) and/or scFvs, was evaluated. Biotin-redirected dcAv.BBIR T cells secrete IFNγ cytokine when stimulated with immobilized biotinylated molecules: in vivo biotinylated scFv (referred to as a biobody) (Green et al., 1973, Biochem. J. 133:687-700) or chemically biotinylated-IgG1 (Bio-IgG1), but not against unlabeled scFv or IgG1 (FIG. 2C). In contrast, mcAv.BBIRz and GFP transduced T cells do not show specific immune-reactivity. The lack of immune-recognition of biotin by mcAv.BBIR-z is consistent with the known poor affinity between biotin and monomeric avidin (Kd=10$^{-4}$) (Green et al., 1973, Biochem. J. 133:687-700) High affinity binding of avidin to biotin is achievable upon avidin dimerization (Kd=10$^{-7}$) or tetramization (Kd=10$^{-14}$) (Laitinen et al., 2001, J. Biol. Chem. 276:8219-8224). Accordingly, only the dcAv.BBIR retains specificity and affinity sufficient for immune-recognition, and was utilized for further assays. To determine the level of biotinylated antibody necessary to trigger BBIR activation, primary T cells transduced with dcAv.BBIR-z or dcAv.BBIR-28z were stimulated by different concentrations of immobilized biotinylated-IgG1 (Bio-IgG1). T cells expressing dcAv.BBIR-z or dcAv.BBIR-28z specifically react against immobilized biotinylated-IgG1 at the ing level (FIG. 2D). Importantly, incorporation of the CD28 co-stimulatory module into dcAv.BBIR-28z allows transduced cells to secrete more IFNγ than dcAv-BBIR-z after immobilized biotin stimulation.

Figures 3A, 3B, 3C:
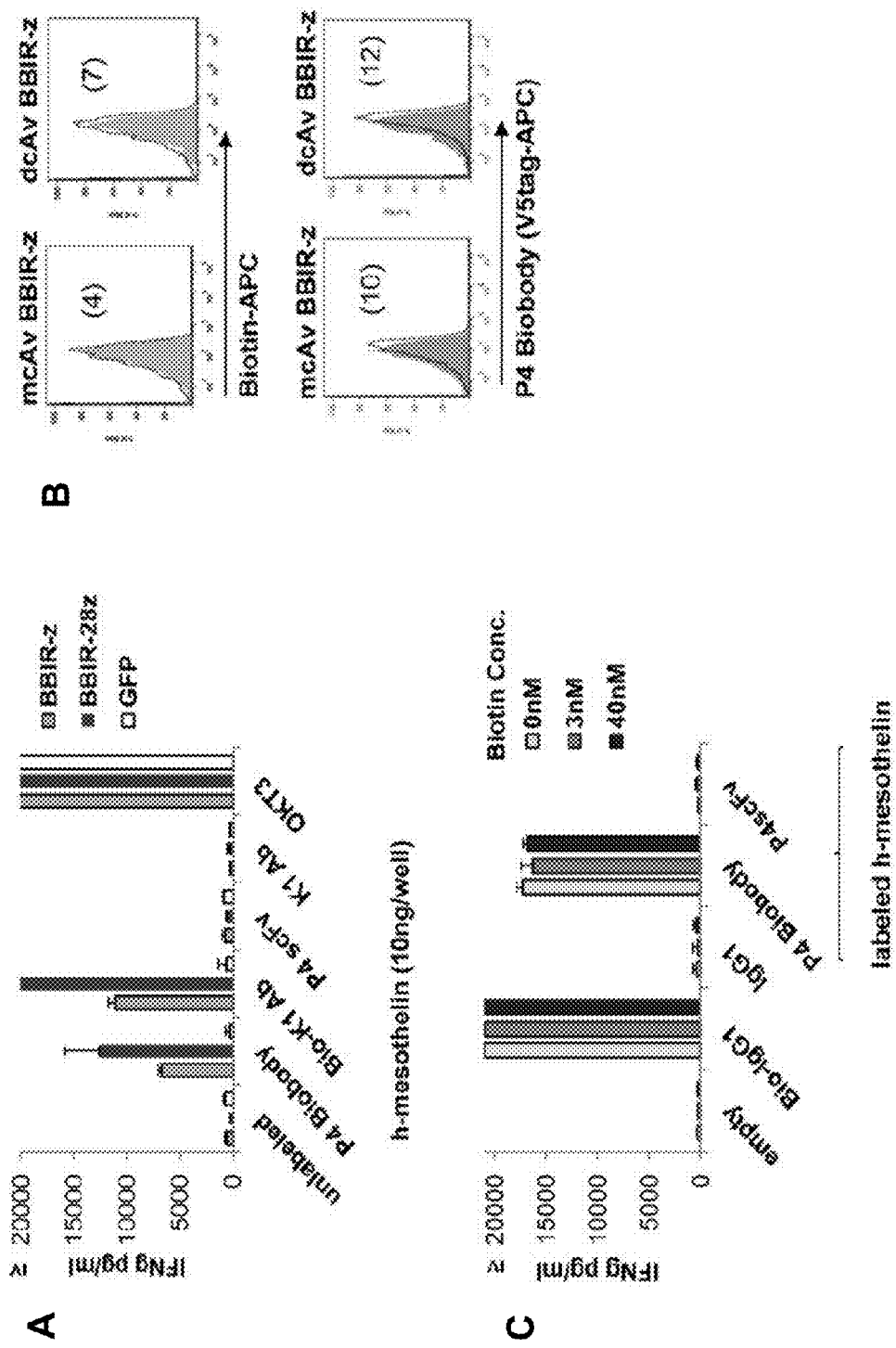
FIGS. 3A-3D, depicts how BBIR⁺ T cells exhibit specific effector functions. FIG. A is a graph depicting how BBIRs respond against immobilized human mesothelin protein when redirected with biotinylated anti-mesothelin scFv or antibody (P4 Biobody and Bio-K1 Ab, respectively). dcAv.BBIR-z, dcAv.BBIR-28z T cells, or control GFP cells ($10^5$ cells per well) were incubated with 10 ng of plate-immobilized mesothelin and with either biotinylated or not, anti-mesothelin antibodies or scFvs (0.1 µg/mL). Overnight culture supernatants were analyzed for human IFNγ cytokine by ELISA. Data represent the means±SD for 3 different experiments.

BBIR T cells are also effective in generating specific, but indirect, immune responses against immobilized protein antigens via intermediate interaction with bound biotinylated antigen specific Abs or scFvs. BBIR cells are redirected and produce IFNγ in response to immobilized mesothelin protein-antigen via engaging biotinylated anti-mesothelin specific molecules, Bio-K1 Ab and P4 Biobody (Scholler et al., 2006, J. Immunol. Methods 317:132-143; Bergan et al., 2007, Cancer Lett. 255:263-274), independently (FIG. 3A). Importantly, neither dcAv.BBIR nor control GFP transduced cells react against mesothelin protein when left unlabeled or painted with non-biotinylated K1 Ab or P4scFv, demonstrating the need for biotin recognition. Compared to BBIR-z, higher levels of IFNγ are observed in cultures of stimulated dcAv.BBIR-28z T cells, where CD28 co-stimulation is incorporated (FIG. 3A). This is consistent with the notion that for robust activation, T cells require two simultaneous signals: an antigen-specific signal provided through TCR/CD3, and a secondary co-stimulatory signal via CD28 co-receptor ligation (Salomon et al., 2001, Annu. Rev. Immunol. 19:225-252; Koehler et al., 2007, Cancer Res. 67:2265-2273). Direct stimulation through the TCR/CD3 alone commonly results in anergy, or antigen induced cell death, and may represent a problem for conventional bispecific-antibodies. Although BBIRs also require an intermediate biotinylated molecule for redirected antigen specificity, incorporation of a co-stimulatory domain into BBIR vectors successfully resolves this issue.

Figure 7:
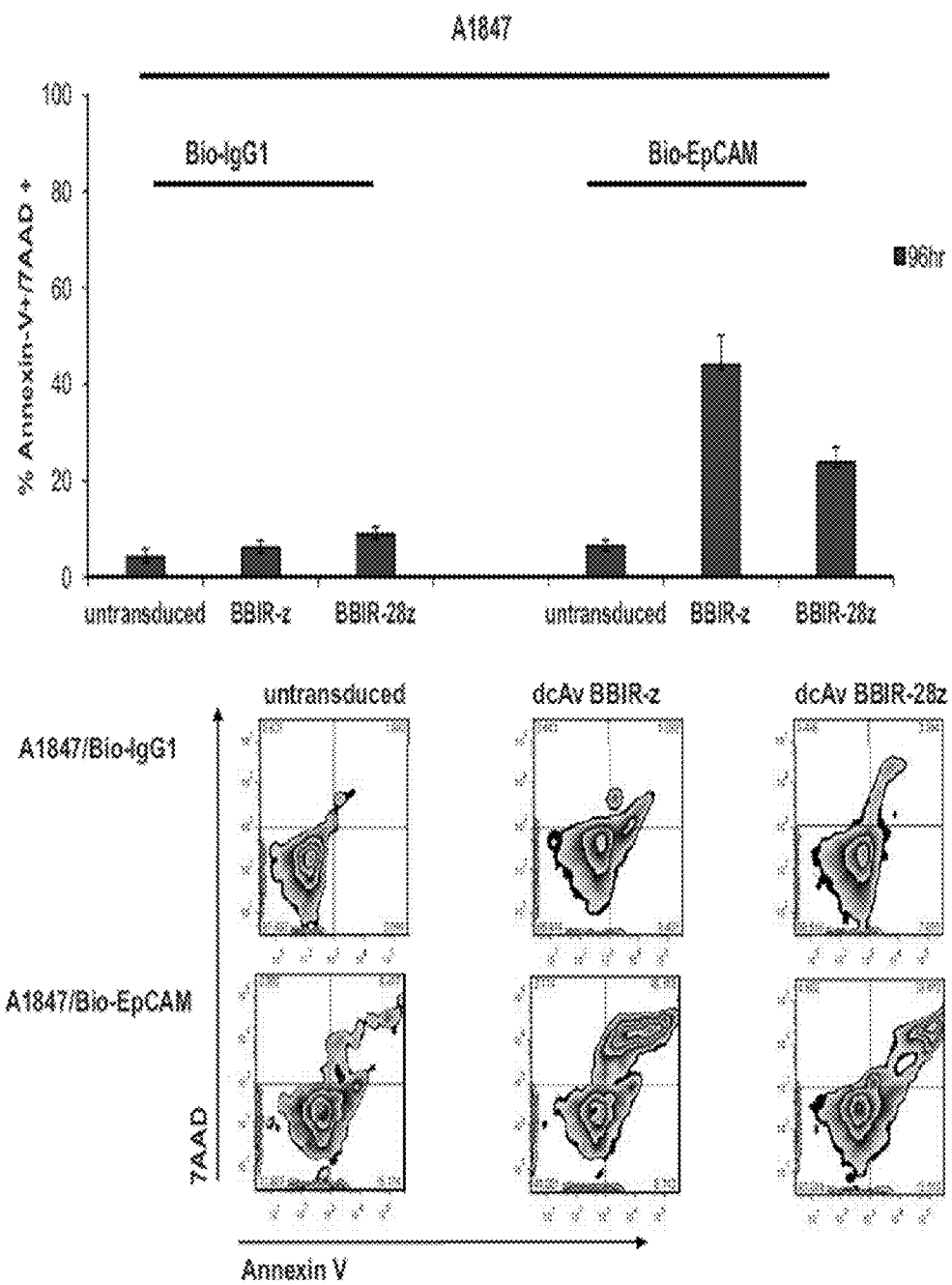
FIG. 7 depicts the CD28 co-stimulation protects against antigen-induced cell death (upper panel). Annexin V and 7-AAD staining of T cells (untransduced, BBIR-z and BBIR-28z) following 72 h (grey bars) and 96 h (black bars) co-culture with A1847 at an E:T ratio 1:1, painted with either Bio-IgG1 or Bio-EpCAM antibodies. Apoptosis was quantified as a percentages of apoptotic cells-Annexin V+ and 7AAD+ (means±SEM; n=3). The lower panel depicts Annexin V/7-AAD assay plots showing T cells after 96 h co-culture with A1847 cell line labeled with biotinylated IgG1 (Bio-IgG1) (top panels) and biotinylated EpCAM specific (Bio-EpCAM) antybodies, at an E:T ratio of 1:1. One representative FACS analysis is shown (n=3).

The possibility of loading biotinylated antigen-specific molecules onto BBIRs in order to arm them against selected antigens was tested. Flow cytometric analysis using biotin-APC or antimesothelin P4 Biobody for loading was performed (FIG. 3B). Neither mcAv nor dcAv.BBIR cells retain biotinylated molecules on their surface after loading, indicating that although the affinity of the dcAv.BBIR permits specific immune-recognition of immobilized biotin, it is insufficient for stable binding, and postulates the potential use of BBIRs for sequential antigen targeting. Consistent with these results, dcAv.BBIR T cells loaded with biotinylated molecules and then washed do not produce IFNγ in response to specific antigen stimulation (FIG. 7).

An important issue concerning biotin-avidin based therapies is the possible effect of soluble biotin on the ability of BBIRs to recognize membrane-bound biotinylated-Abs, since biotin is present in human plasma in levels of 0.2-2 nM (Stratton et al., 2010, Am. J. Clin. Nutr. 92:1399-1405) The influence of soluble biotin on BBIRs reactivity was evaluated by measurement of IFNγ production against immobilized antigen (Biotinylated-IgG1, or mesothelin painted with Bio-K1 or P4 Biobody) Immobilized biotinylated-IgG1, as well as recombinant human mesothelin, painted with P4 Biobody activated dcAv.BBIR-28z T cells, even in the presence of soluble biotin at the concentration 20 times higher than physiological, 40 nM (FIG. 3C). Notably, soluble biotin alone did not cause antigen-independent activation of BBIRs even at supraphysiological levels.

Figure 3D:
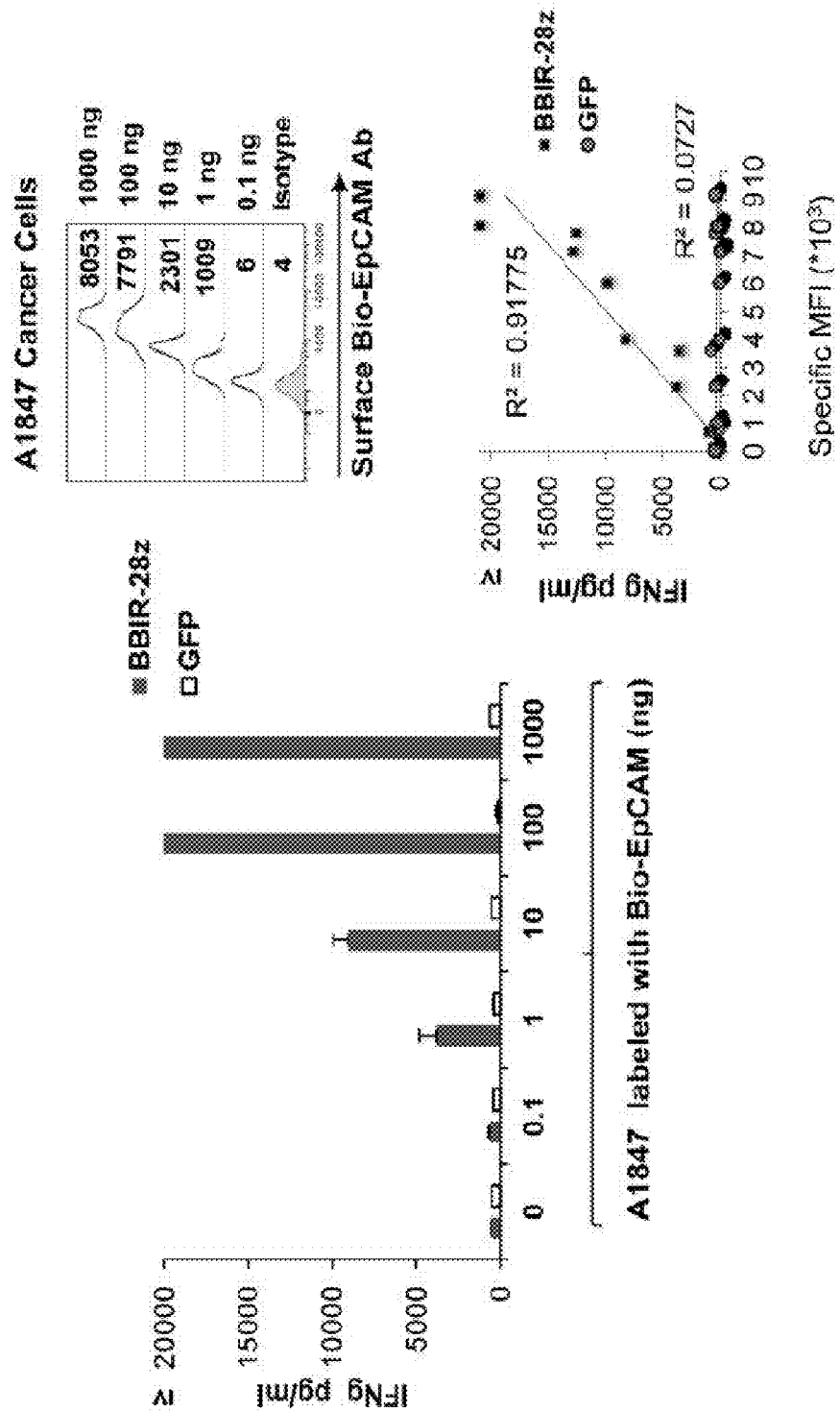
Figure 8:
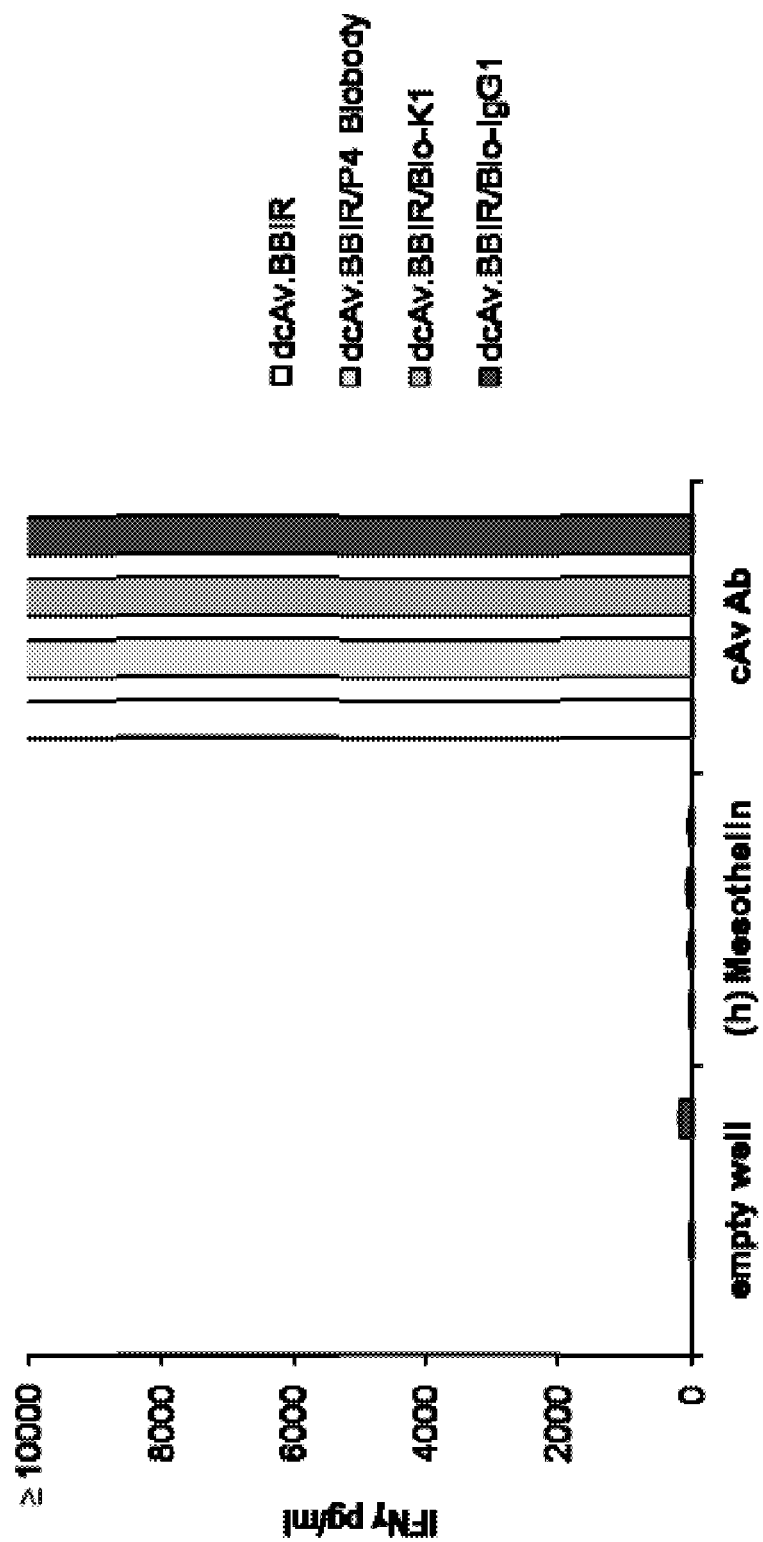
FIG. 8 is a graph depicting how BBIR-z T cells loaded with biotinylated molecules and subsequently washed do not produce IFNγ in response to specific antigen stimulation. Following 45 min incubation at 37° C. with 1 µg/ml of mesothelin specific biotinylated antybodies; P4 Biobody or K1 and control Bio-IgG1 antibody, BBIR-z T cells were washed with PBS and tested against plate-immobilized human mesothelin (10⁵ cells/10 ng mesothelin/well). After overnight incubation, culture supernatants were analyzed for human IFNγ cytokine by ELISA. Concentration of IFNγ is expressed in pg/ml (means±SEM; n=3).

The effectiveness of BBIR modified T cells in generating specific immuneresponses against TAAs expressed on the tumor cell surface was examined by culturing BBIRs with the human ovarian cancer cell line, A1847, painted with Bio-EpCAM Ab. In the co-culture with EpCAM-positive A1847 cells, dcAv.BBIR-28z T cell activation was induced when biotinylated anti-EpCAM Ab is added in a dose-dependent fashion (FIG. 3D). Moreover, a linear correlation existed between the levels of attached biotinylated Ab, presented as specific MFI, and the level of IFNγ secretion by BBIR, but not GFP, T cells (FIG. 3D). Specific recognition and reactivity against A1847 was detectable when targeted against a single antigen using Bio-EpCAM Ab, even at 0.1 ng/ml concentration. Consistent with enhanced effector function (FIGS. 2D and 3A), increased T cell survival is observed in cultures of antigen-stimulated dcAv.BBIR-28z T cells, where CD28 co-stimulation is incorporated, compared to BBIR-z (FIG. 8).

Figure 4:
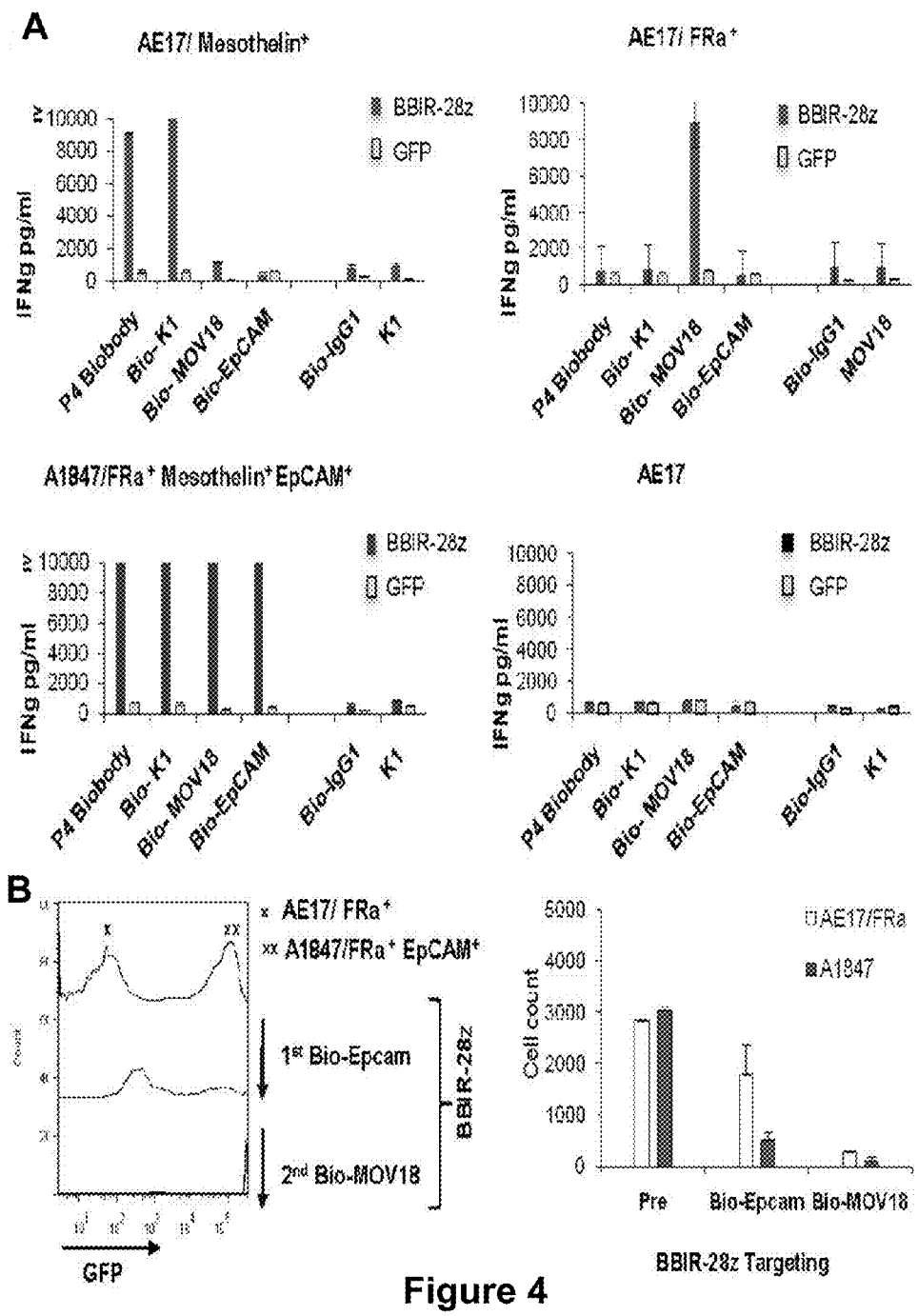
FIG. 4, comprising
Figure 9:
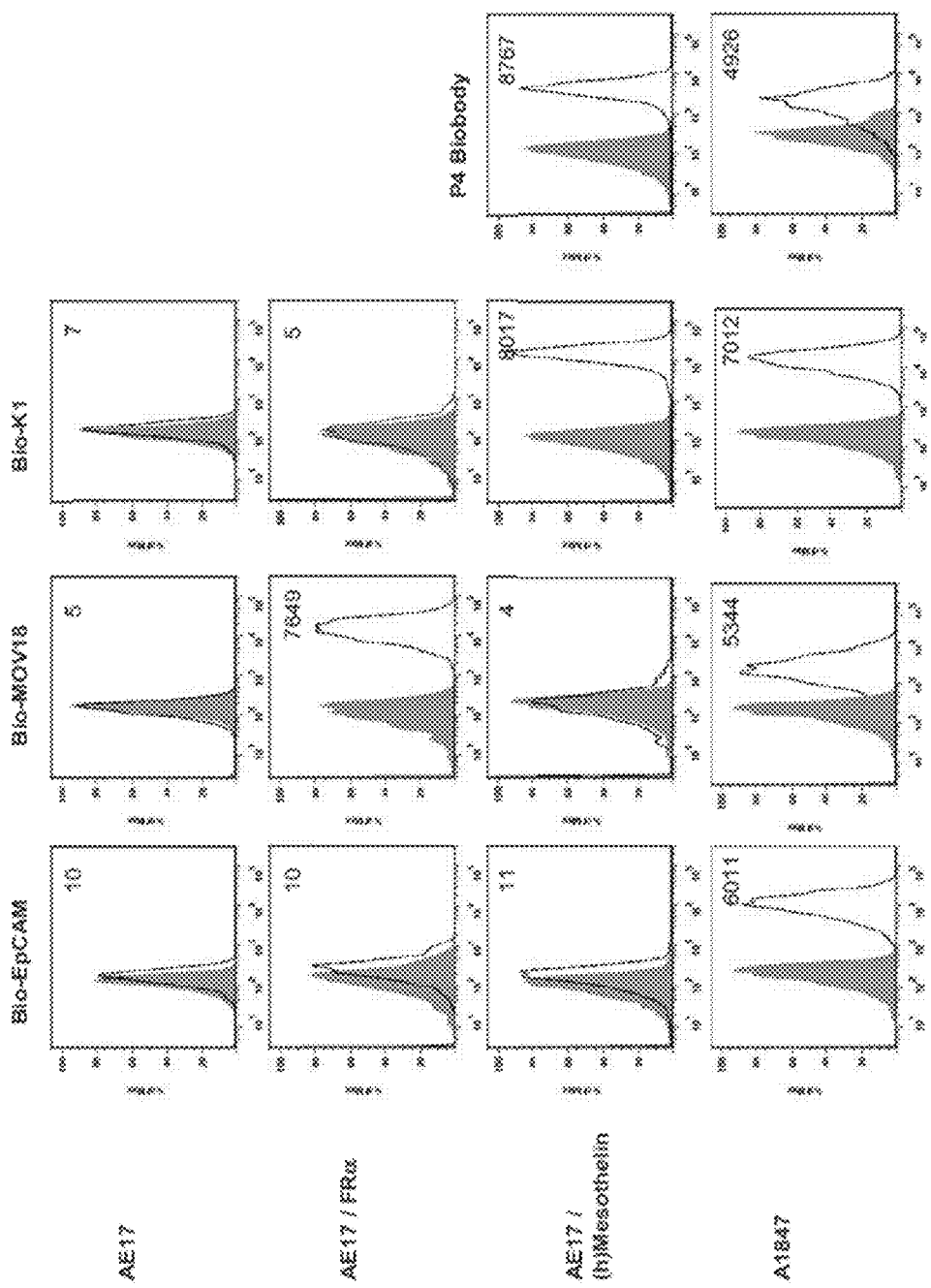
FIG. 9 is a series of graphs depicting Flow Cytometry analysis of an antigen surface expression on mouse AE17 cell lines transduced to express human FRα or mesothelin and human ovarian cancer cell line, A1847. FRα-specific mAb Mov18, EpCAM-specific and mesothelin-specific K1 antibody and P4 Biobody were used to measure antigen expression on tumor cell lines (open empty histogram), compared to a matched isotype Ab control (filled gray histogram). Numbers within plots refer to specific mean fluorescent intensity (MFI).
Figure 10:
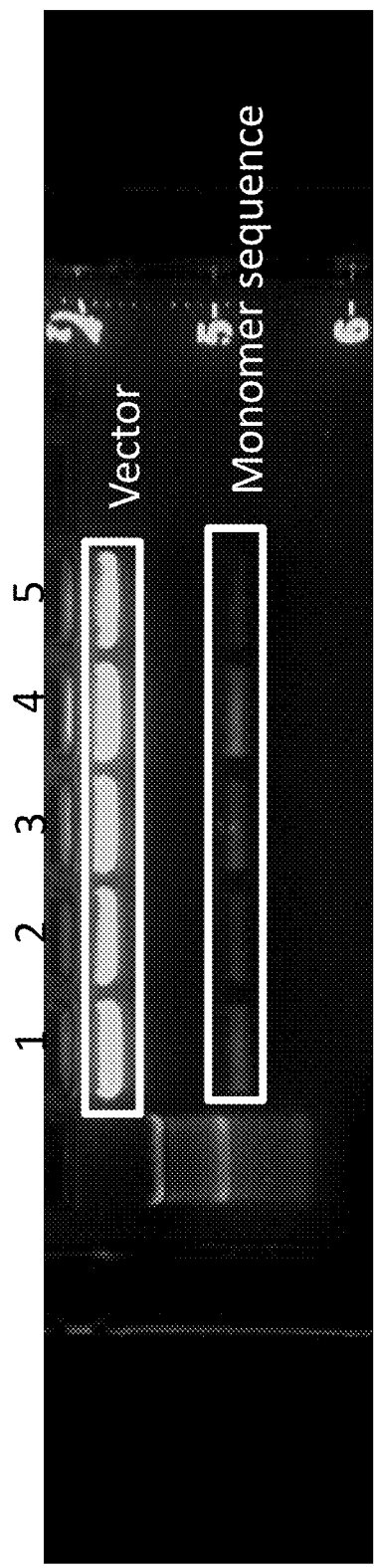
FIG. 10 is an image demonstrating the digestion of mcAv constructs by restriction endonucleases. Lower band represents a monomer chicken Avidin; upper band represents linearized vector pELNS or pCLPS respectively. 500 ng of each vector was digested with BamH1 and NheI enzymes for 2 hrs at 37° C. Lanes 1-5 depict mcAv pCLPS, mcAv CD3ζ GFP pELNS, mcAv 28ζ GFP pELNS, mcAv 28ζ GFPpELNS, mcAv BBζ GFP pELNS, respectively.
Figure 11:
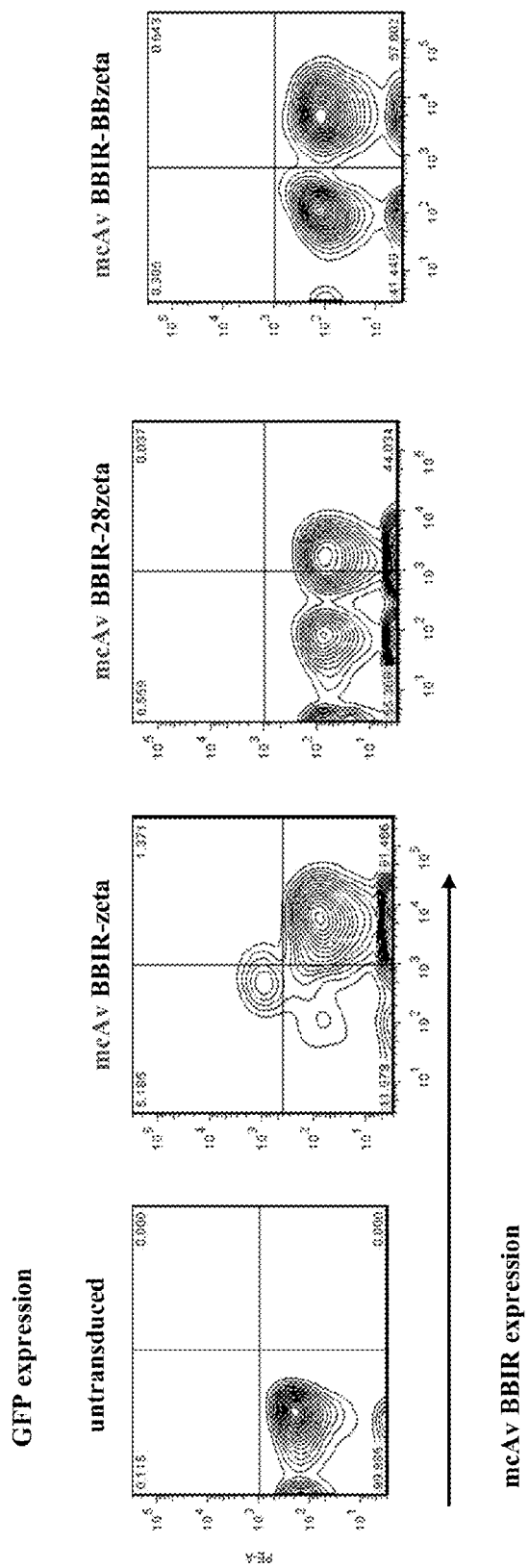
FIG. 11 is an image demonstrating the transduction efficiency in T cells after lentiviral transfer of mcAV BBIR (pELNS GFP 2A vectors). Biotin Binding Immune Receptor expression was detected via GFP expression for mcAv constructs, 5 days after transduction with lentivirus compared to untransduced T cells. Percentage of CAR transduction is indicated. The results demonstrate that primary human T cells can be efficiently transduced to express mcAV BBIR (monomer) on their cell surface.
Figure 12:
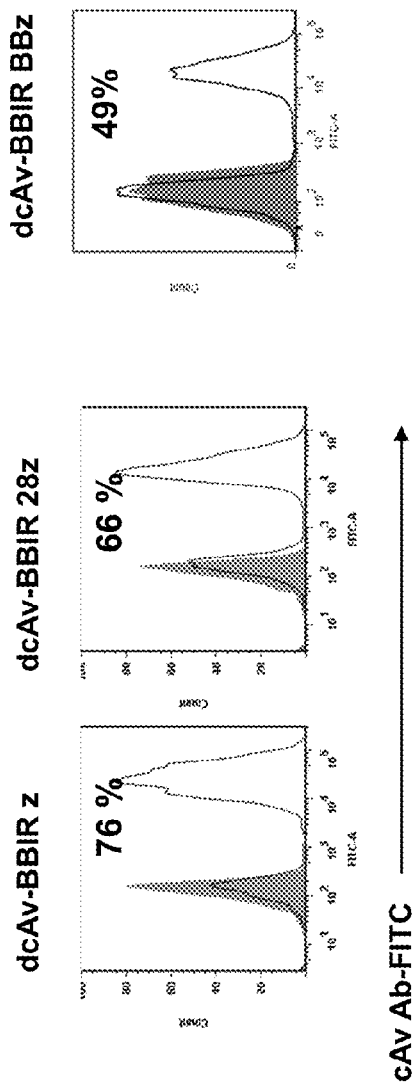
FIG. 12 is an image demonstrating that primary human T cells can be efficiently transduced to express dcAV BBIR (dimer) on their cell surface. Biotin Binding Immune Receptor expression (open histograms) was detected via anti-avidin antibody for dcAV constructs staining 5 days after transduction with lentivirus compared to untransduced T cells (grey filled histograms). Percentage of CAR transduction is indicated.
Figure 13:
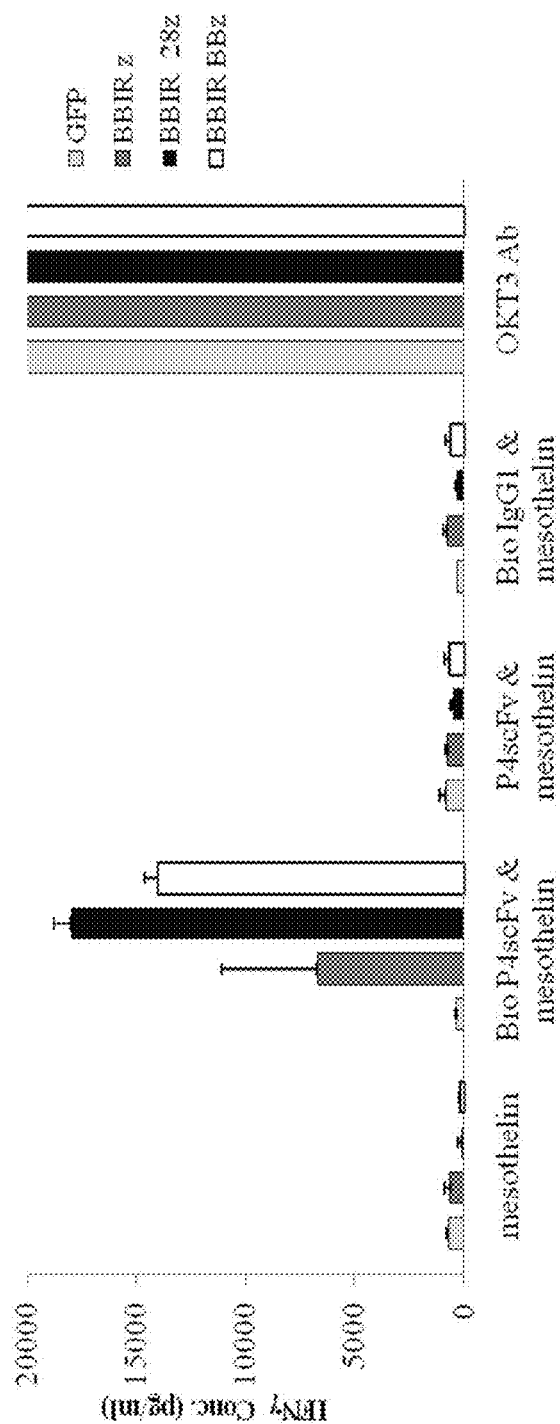

Whether the universality of the BBIR platform would allow BBIR-modified T cells to generate specific immune response against variable TAAs expressed on the cancer cell surface was examined. BBIR T cells were tested for function against a panel of established cancer cell lines that express varying cell surface antigens, including A1847 (mesothelin$^+$, folate binding protein/FRα$^+$, EpCAM$^+$); antigen-negative AE17 mouse mesothelial cells non-modified or transduced to express either human mesothelin or human FRα (FIG. 9). Binding of biotinylated Abs to mesothelin, FRα (Bio-MOV18) or EpCAM on the respective tumor cell surface enabled specific immune-recognition of various tumor cells with non-overlapping antigen expression in an MHC-independent manner and triggers secretion of IFNγ by BBIR T cells (FIG. 4A). To further evaluate the flexibility of BBIR platform, BBIRs were tested to determine if they could be sequentially redirected from one antigen to another antigen of distinct specificity. GFP-transduced A1847 cells were mixed at a 1:1 ratio with the EpCAM-negative AE17/FRα$^+$ cells and then co-cultured with BBIR T cells. Here, BBIR T cell specificity can be redirected from first targeting EpCAM$^+$ tumors (A1847/GFP), via Bio-EpCAM Ab, to additionally targeting tumor cells expressing FRα but not EpCAM (AE17/FRα$^+$), by secondarily adding a biotinylated Ab with FRα specificity (Bio-Mov18) to the culture (FIG. 4B). Similar results were observed after redirecting BBIRs in the reverse sequence, targeting FRα first followed by EpCAM. These observations are consistent with the versatility of the BBIR platform.

Figure 5:
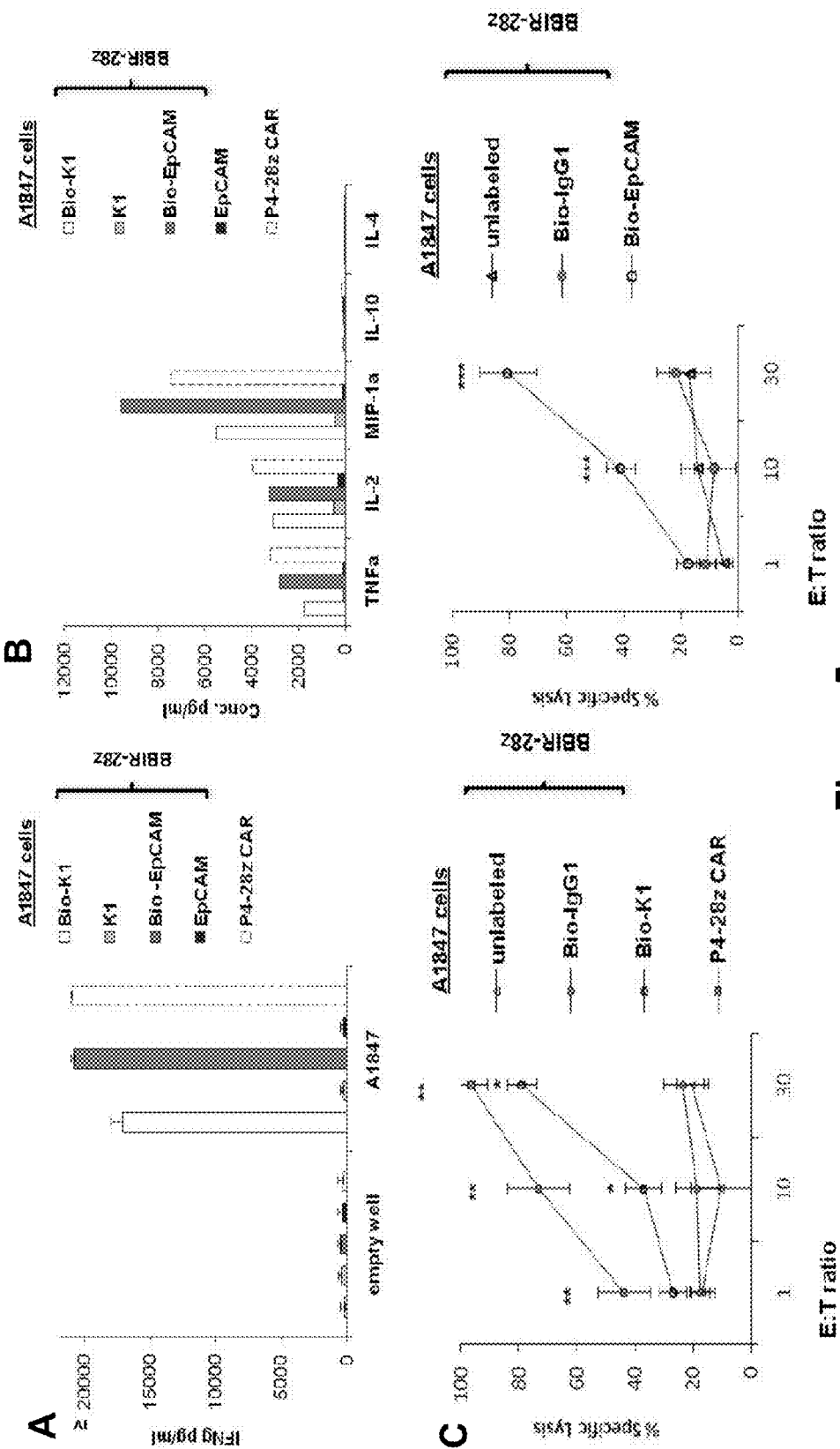
FIG. 5, comprising

The in vitro anti-cancer immune response of primary human T lymphocytes expressing a conventional CAR was compared to those retargeted with dcAv.BBIR and biotinylated molecules. Antimesothelin P4-28z CAR$^+$ T cells stimulated with ovarian cancer cells expressing mesothelin (A1847) preferentially secreted high levels of Th1 cytokines including IFNγ, TNFα, and IL-2 upon tumor encounter (Lanitis et al., 2012, Mol. Ther. 20:633-643). Here, T cells expressing conventional anti-mesothelin P4-28z CAR or dcAv.BBIR-28z redirected against mesothelin via Bio-K1 (anti-mesothelin) Ab tumor cell labeling secrete Th1 cytokines at similar levels in co-cultures with A1847 (FIG. 5A). In line with previous experiments (FIG. 4A), BBIR T cells exhibit immune-recognition of A1847 cell line upon engaging biotinylated Abs specific to either human mesothelin or EpCAM on the cancer cell surface.

To interrogate antigen-specific cytolytic potential, dcAv-BBIR-28z T cells were co-cultured with mesothelin$^+$ EpCAM$^+$ A1847 cancer cells painted with biotinylated or non-biotinylated Abs specific to these molecules. In chromium release assays, BBIRs specifically lysed A1847 cancer cells when painted with either Bio-K1 or Bio-EpCAM Abs but not non-biotinylated counterparts (FIG. 5B). Thus, human T cells expressing dcAv.BBIR specifically can recognize various painted antigens and exert cytotoxic activity in vitro. Control GFP transduced cells exhibit no substantial cytotoxic activity against the same target cells, consistent with the exclusion of the possibility of nonspecific lysis.

Figure 6:
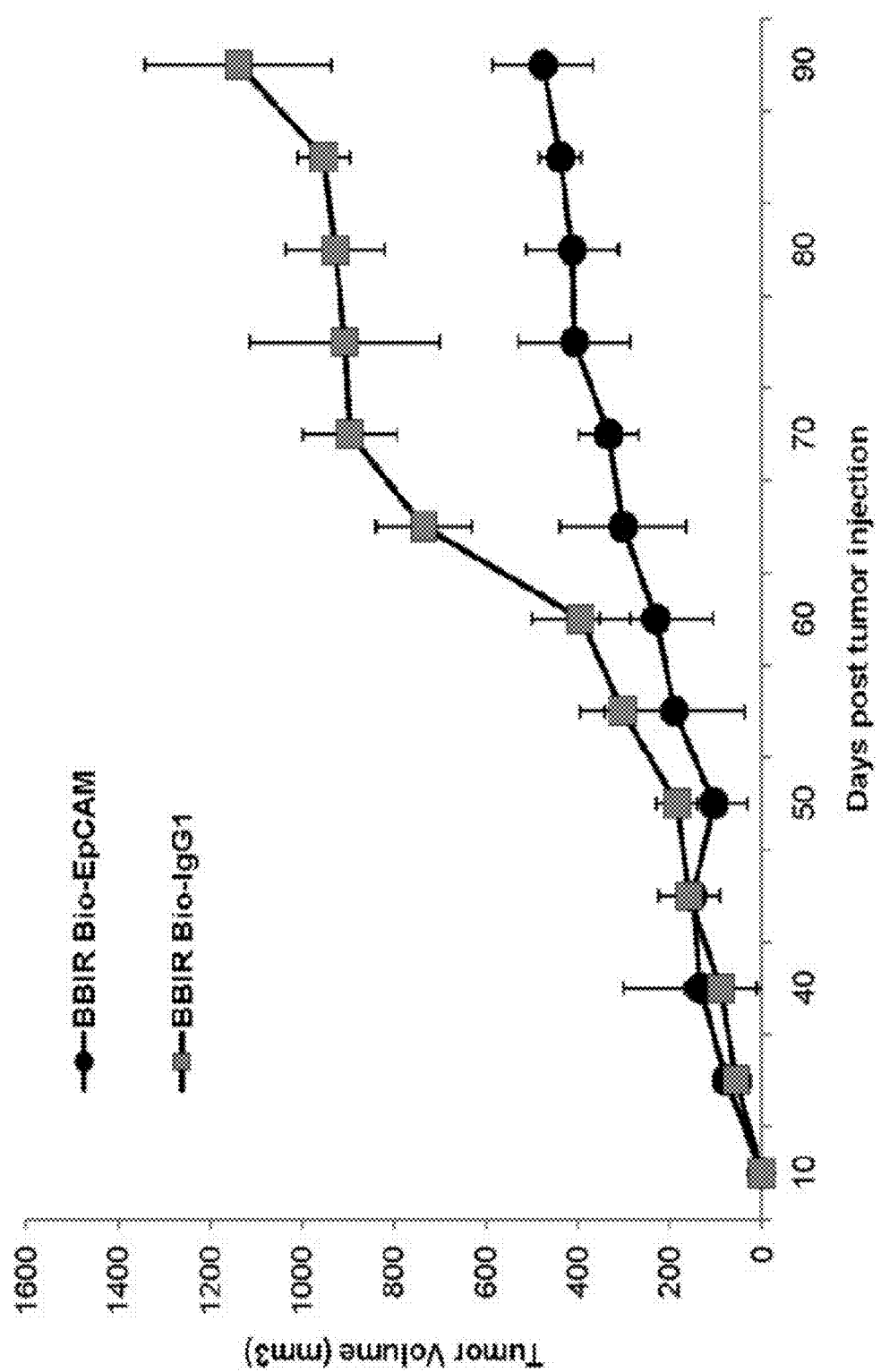
FIG. 6 is a graph depicting dcAv.BBIR-28z⁺ T cells control tumor growth in an ovarian cancer xenograft model. A total of 5×10⁶ A1847 tumor cells were inoculated subcutaneously in the flank of NSG mice. To test the therapeutic efficacy of BBIR⁺ T cells, mice bearing an established tumor (≥150 mm³) were inoculated IT with 6×10⁶ BBIR⁺ T cells and Bio-EpCAM Ab (100 ng) or BBIR⁺ T cells and Bio-IgG1 Ab (100 ng) on days 45, 48, and 51. Additional antibody-only injections (100 ng) were given on days 56 and 60. Tumor growth was then monitored as tumor diameter per day. Data represent the means±SD of 4 mice for each panel presented. P≤0.005 comparing BBIR⁺/Bio-EpCAM and BBIR⁺/Bio-IgG1 group.

The antitumor efficacy of BBIR T cells was evaluated in a xenograft model of large, established human cancer Immunodeficient NOD/SCID/IL-2Rγcnull (NSG) mice were inoculated s.c. with firefly luciferase (fLuc) transfected EpCAM+ A1847 human ovarian cancer cells on the flank and received intratumoral injections of BBIR T cells and biotinylated Ab when tumors were ≥150 mm³ in size. Tumors progressed beyond the time of T cell transfer in mice receiving injections of a control biotinylated antibody, Bio-IgG1, whereas tumor growth was significantly delayed in similarly treated mice receiving Bio-EpCAM Ab, consistent with the concept that the introduction of an antigen-specific biotinylated antibody induces anti-tumor activity of BBIR T cells in vivo (FIG. 6).

The BBIR platform represents a "universal immune receptor" approach for the targeting of gene-modified T cells to diverse and multiple antigens via interaction with antigen bound biotinylated molecules, either simultaneously or sequentially. Evidence is provided that BBIR expressing T cells generate robust immune responses in vitro against immobilized or cell surface expressed mesothelin marked with biotinylated anti-mesothelin P4scFv, indicating utility of the BBIR platform in the screening of Ab and scFv candidates for possible UnivIR construction. Additionally, both BBIR with P4 Biobody and conventional P4scFv-based CAR exhibit reactivity in vitro. Though validated with biotinylated Ab and scFvs as antigen targeting molecules as described herein, the platform may be broadened in application to include ligand/receptors, oligonucleotides, and/or single chain TCRs. Additionally, the binding partners themselves may be substituted for those with higher affinity or more specific binding to the targeting molecule. Theoretically, BBIR can redirect T cell function against virtually any antigen for which a specific targeting agent exists. The proof-of-concept findings, coupled with recent results showing that UnivIR redirected allogeneic T cells can be used as universal "off-the-shelf" effectors for cancer therapy, offer the potential to substantially broaden availability of highly personalized, potent redirected T cells to patients in future cancer immunotherapy trials.

Based on the disclosure presented herein, experiments can be designed to identify the optimal antibody dose required for efficient tumor-labeling and BBIR recognition, as well as determining the impact of BBIR affinity to targets on the antitumor activity. The finding that preloading or arming of BBIR+ T cells with soluble biotinylated scFV (or biotin-APC) is not sufficient for immune recognition represents a possible advantageous feature of the BBIR system particularly given the presence of natural biotin present in human plasma that might otherwise preclude antigen-independent activation of BBIRs. Further, cancer regression and high level T cell persistence has been observed in patients receiving autologous transfer of T cells engineered to express a xenogeneic TCR or CAR when combined with host lymphodepleting preconditioning (Kochenderfer et al., 2010, Blood 116:4099-4102; Porter et al., 2011, N. Engl. J. Med. 365:725-733; Johnson et al., 2006, J Immunol 177:6584-6559). Importantly, chicken avidin is reported to have low immunogenic potential, though conflicting reports exist in the literature (Samuel et al., 1996, J. Nucl. Med. 37:55-61; Paganelli et al., 1991, Cancer Res. 51:5960-5966).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. An isolated nucleic acid encoding a biotin binding immune receptor (BBIR), wherein the BBIR comprises an extracellular label binding domain comprising a dimerized avidin domain, a transmembrane domain, a T cell receptor signaling domain, wherein the label binding domain binds to a biotinylated antigen, and further wherein the nucleic acid comprises a nucleic acid sequence selected from the group consisting of SEQ ID NOs: 11, 12 and 13.

2. The isolated nucleic acid of claim 1, wherein the biotinylated antigen is selected from the group consisting of a tumor antigen, a self-antigen, a viral antigen, and any combination thereof.

3. A cell comprising a nucleic acid encoding a biotin binding immune receptor (BBIR), wherein the BBIR comprises an extracellular label binding domain comprising a dimerized avidin domain, a transmembrane domain, a T cell receptor signaling domain, wherein the label binding domain binds to a biotinylated antigen, and further wherein the nucleic acid comprises a nucleic acid sequence selected from the group consisting of SEQ ID NOs: 11, 12 and 13.

4. The cell of claim 3, wherein the cell is selected from the group consisting of a T cell, a Natural Killer (NK) cell, a cytotoxic T lymphocyte (CTL), and a regulatory T cell.

5. The cell of claim 3, wherein the cell is activated when the label binding domain binds to its corresponding biotinylated antigen.

6. A vector comprising a nucleic acid encoding a biotin binding immune receptor (BBIR), wherein the BBIR comprises an extracellular label binding domain comprising a dimerized avidin domain, a transmembrane domain, a T cell receptor signaling domain, wherein the label binding domain binds to a biotinylated antigen, and further wherein the nucleic acid comprises a nucleic acid sequence selected from the group consisting of SEQ ID NOs: 11, 12 and 13.

* * * * *

UNITED STATES PATENT AND TRADEMARK OFFICE
CERTIFICATE OF CORRECTION

| | | |
|---|---|---|
| PATENT NO. | : 9,708,384 B2 | Page 1 of 1 |
| APPLICATION NO. | : 14/346612 | |
| DATED | : July 18, 2017 | |
| INVENTOR(S) | : Nathalie Scholler, Katarzyna Urbanska and Daniel J. Powell | |

It is certified that error appears in the above-identified patent and that said Letters Patent is hereby corrected as shown below:

In Column 1, after the paragraph, CROSS-REFERENCE TO RELATED APPLICATION and before the title BACKGROUND OF THE INVENTION, please insert the following paragraph:

--STATEMENT REGARDING FEDERALLY SPONSORED RESEARCH OR DEVELOPMENT
This invention was made with government support under grant no. R21 CA152540 and R01 CA168900 awarded by the National Institutes of Health. The government has certain rights in the invention.--

Signed and Sealed this
Twenty-third Day of January, 2018

Joseph Matal
*Performing the Functions and Duties of the
Under Secretary of Commerce for Intellectual Property and
Director of the United States Patent and Trademark Office*